United States Patent
Wilson

(10) Patent No.: US 9,565,812 B2
(45) Date of Patent: Feb. 14, 2017

(54) LED LIGHT TIMING IN A HIGH GROWTH, HIGH DENSITY, CLOSED ENVIRONMENT SYSTEM

(71) Applicant: AquaHarvest Technologies, Inc., Medfield, MA (US)

(72) Inventor: James G. Wilson, Medfield, MA (US)

(73) Assignee: Crop One Holidings, Inc., Millis, MA (US)

( * ) Notice: Subject to any disclaimer, the term of this patent is extended or adjusted under 35 U.S.C. 154(b) by 162 days.

(21) Appl. No.: 14/200,210

(22) Filed: Mar. 7, 2014

(65) Prior Publication Data

US 2014/0259920 A1    Sep. 18, 2014

Related U.S. Application Data

(60) Provisional application No. 61/784,837, filed on Mar. 14, 2013.

(51) Int. Cl.
| | | |
|---|---|---|
| *A01C 1/02* | (2006.01) | |
| *A01C 1/00* | (2006.01) | |
| *A01G 31/00* | (2006.01) | |
| *A01G 31/02* | (2006.01) | |
| *A01G 7/04* | (2006.01) | |

(52) U.S. Cl.
CPC .............. *A01G 31/02* (2013.01); *A01C 1/00* (2013.01); *A01C 1/02* (2013.01); *A01G 7/045* (2013.01); *Y02P 60/149* (2015.11); *Y02P 60/216* (2015.11)

(58) Field of Classification Search
CPC .............. A01G 1/00; A01G 1/04; A01G 1/02; A01G 1/042; A01G 7/00; A01G 7/02; A01G 9/18; A01G 31/00; A01G 31/02; A01G 31/042; A01G 31/045; A01G 31/047; A01G 31/06
USPC ................. 47/59 R, 60, 61, 62 R, 62 N, 63, 17,47/58.1 SE
See application file for complete search history.

(56) References Cited

U.S. PATENT DOCUMENTS

| | | | | |
|---|---|---|---|---|
| RE31,023 E | * | 9/1982 | Hall, III | A01D 46/24 137/236.1 |
| 5,873,197 A | * | 2/1999 | Rowse | A01C 1/06 47/16 |
| 6,065,245 A | * | 5/2000 | Seawright | A01G 31/00 119/200 |

(Continued)

FOREIGN PATENT DOCUMENTS

| | | |
|---|---|---|
| JP | 2011177127 A | 9/2011 |
| JP | 2012254058 A | 12/2012 |

(Continued)

OTHER PUBLICATIONS

PCT/US2014/021917, International Application Serial No. PCT/US2014/021917, International Preliminary Report on Patentability and Written Opinion mailed Sep. 24, 2015, Crop One Holdings, Inc., 6 Pages.

(Continued)

*Primary Examiner* — Son T Nguyen
(74) *Attorney, Agent, or Firm* — GTC Law Group PC & Affiliates

(57) ABSTRACT

Disclosed herein is a high growth, high density, closed environment growing system and methods thereof. A method of accelerating plant cell growth in a growing system may include adjusting the lighting in accordance with an identified plant growth stage.

20 Claims, 28 Drawing Sheets

(56) References Cited

U.S. PATENT DOCUMENTS

| | | | |
|---|---|---|---|
| 7,565,768 B2* | 7/2009 | Bula | A01H 4/005 47/58.1 LS |
| 2005/0252078 A1* | 11/2005 | Albright | A01G 7/02 47/58.1 LS |
| 2006/0053691 A1 | 3/2006 | Harwood et al. | |
| 2007/0039241 A1* | 2/2007 | Battke | A01G 31/00 47/59 S |
| 2008/0276534 A1* | 11/2008 | Bissonnette | A01G 7/00 47/62 R |
| 2009/0229177 A1* | 9/2009 | Hyde | A01G 7/00 47/1.7 |
| 2009/0260281 A1* | 10/2009 | Conrad | A01C 1/025 47/14 |
| 2009/0272029 A1* | 11/2009 | Aiking | A01G 7/04 47/1.43 |
| 2010/0115830 A1* | 5/2010 | Dube | A01G 7/045 47/17 |
| 2013/0042523 A1 | 2/2013 | Lee et al. | |
| 2013/0198693 A1* | 8/2013 | Jost | G06F 3/04815 715/848 |
| 2014/0115958 A1* | 5/2014 | Helene | A01G 1/001 47/17 |
| 2014/0173769 A1* | 6/2014 | Leyns | A01G 7/00 800/260 |
| 2014/0344100 A1* | 11/2014 | Fok | A01G 31/00 705/26.5 |
| 2015/0230409 A1* | 8/2015 | Nicole | A01G 7/045 47/17 |

FOREIGN PATENT DOCUMENTS

| | | |
|---|---|---|
| KR | 1020110092151 A | 8/2011 |
| WO | 2014159091 A1 | 10/2014 |

OTHER PUBLICATIONS

PCT/US2014/021917, International Application Serial No. PCT/US2014/021917, International Search Report and Written Opinion mailed Jul. 18, 2014, Aquaharvest Technologies, Inc., 9 pages.

* cited by examiner

Figure 2

- (12) SS = Seedling Stress Time => Total # of Hours
- (13) $A_i$ = Ratio factor of turning on and off lights
- (14) $AT_i = A_i * 60$ => Total number of minutes lights ON with the same number of minutes OFF
- (15) $T_s$ = Timing total of light cycles in Phase $A_i$
- (16) $T_s = 1/3\ SS$
- (17) $C_i$ = The total of ON and OFF cycles in a given subphase of $A_i$, whereby one cycle is turning the lights ON and OFF
- (18) $C_i = T_s / 2A_i$
- (19) R = Recommended Lighting Cycles for a given plant species in given hours/day

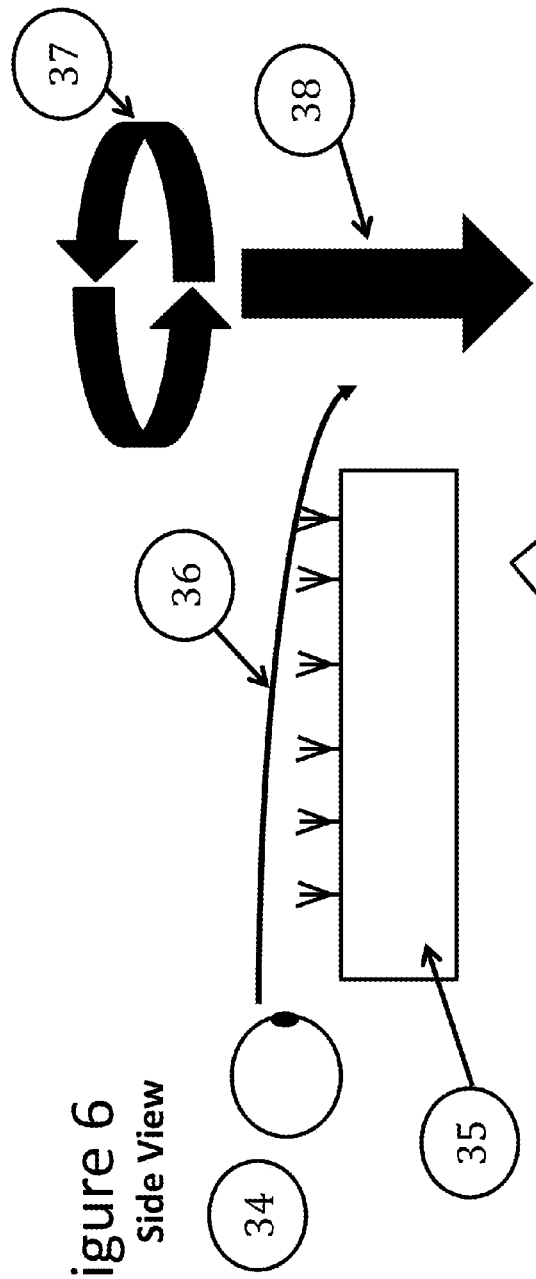
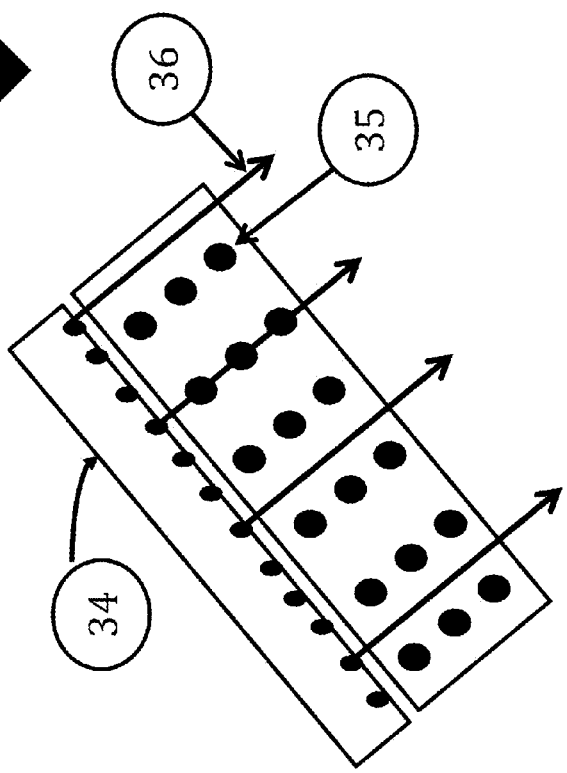
Figure 6
Side View
Figure 7
Top View

Figure 10

Heated Nutrient Equations

- (53) R = Optimal Hydroponic nutrient temperature for a specific plant species.

- (47) Phase $A_1$ => .7 * R
- (48) Phase $A_2$ => .75 * R
- (49) Phase $A_3$ => .8 * R
- (50) Phase B => R
- (51) Phase C => R
- (52) Phase D => .7 * R

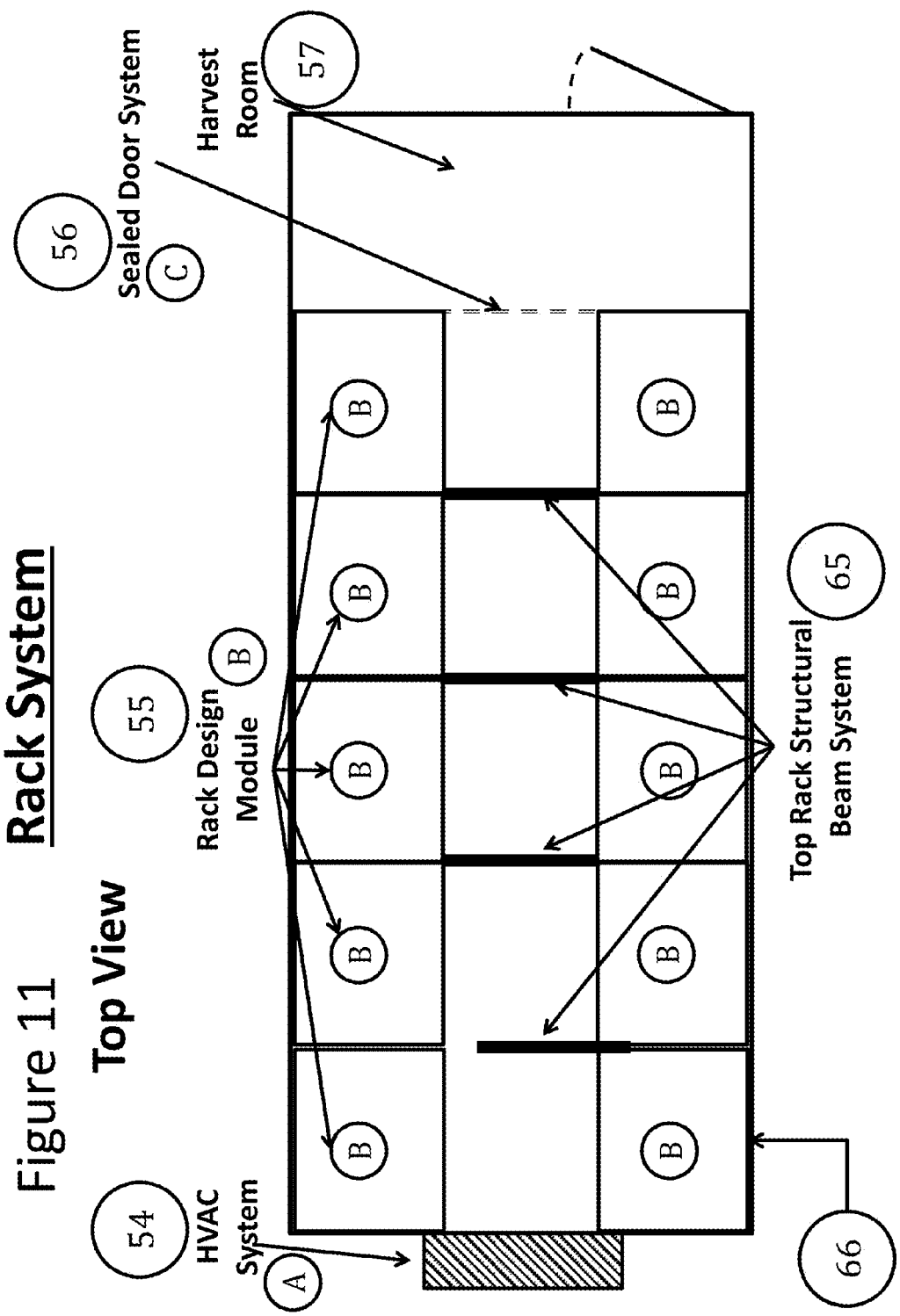

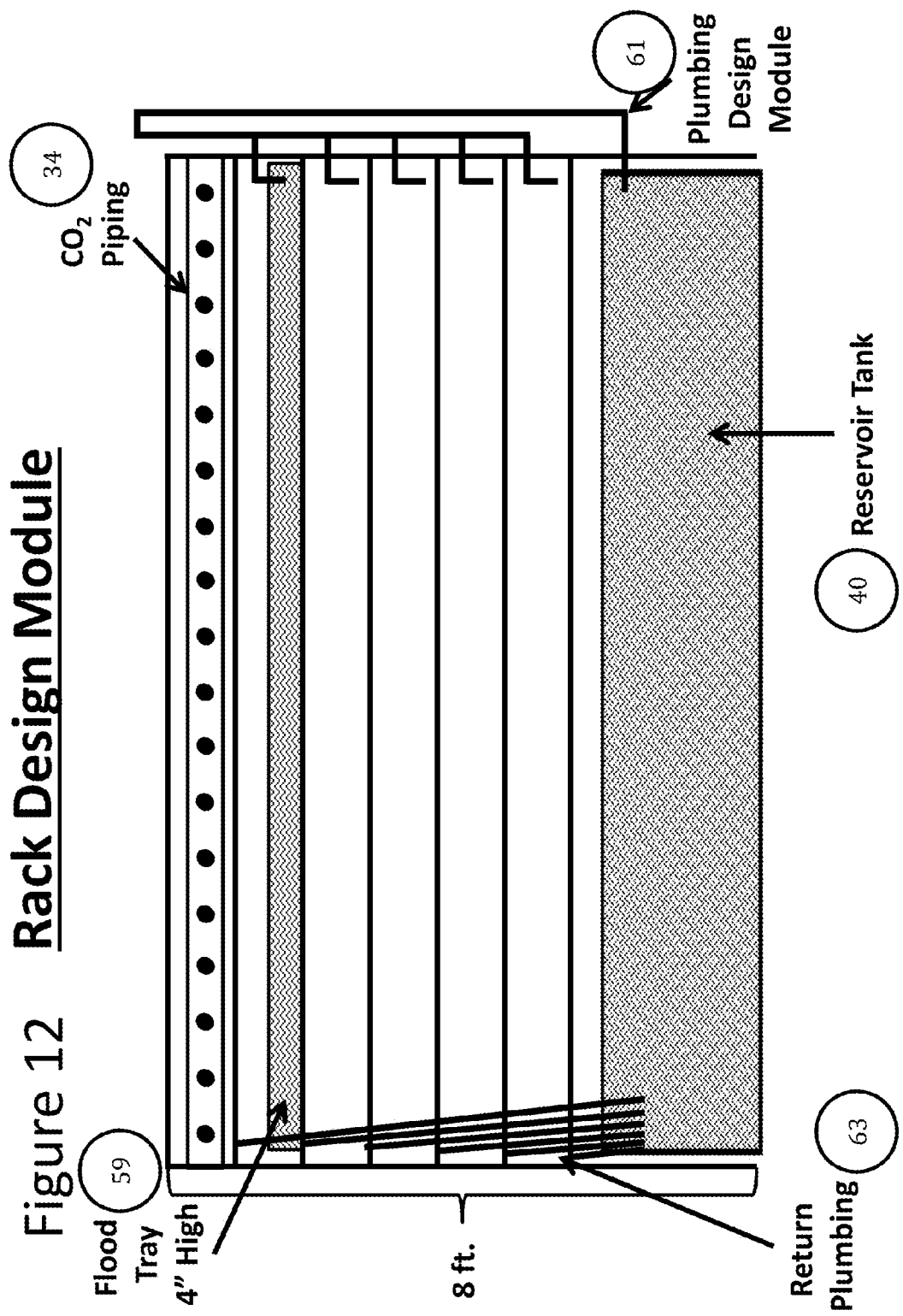
Figure 12 — Rack Design Module

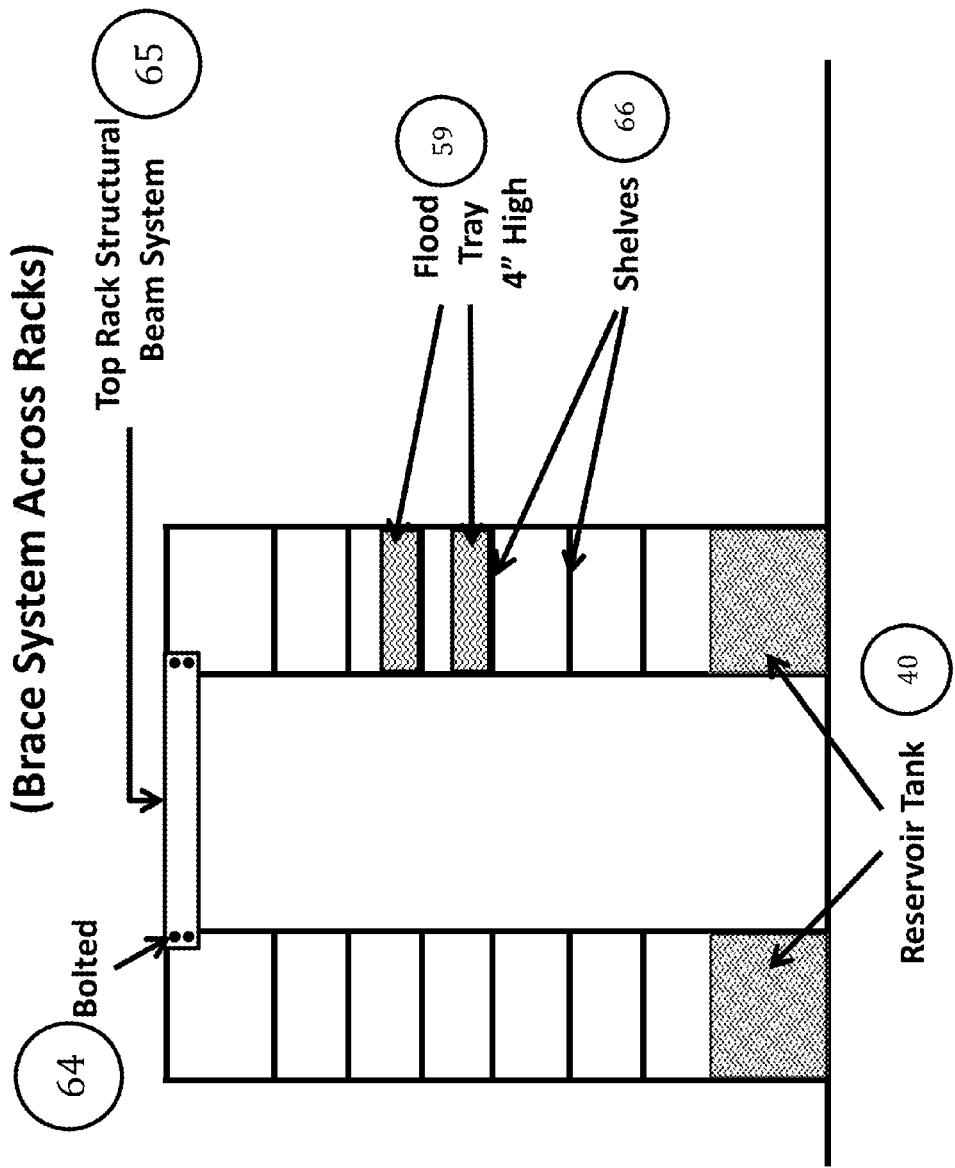

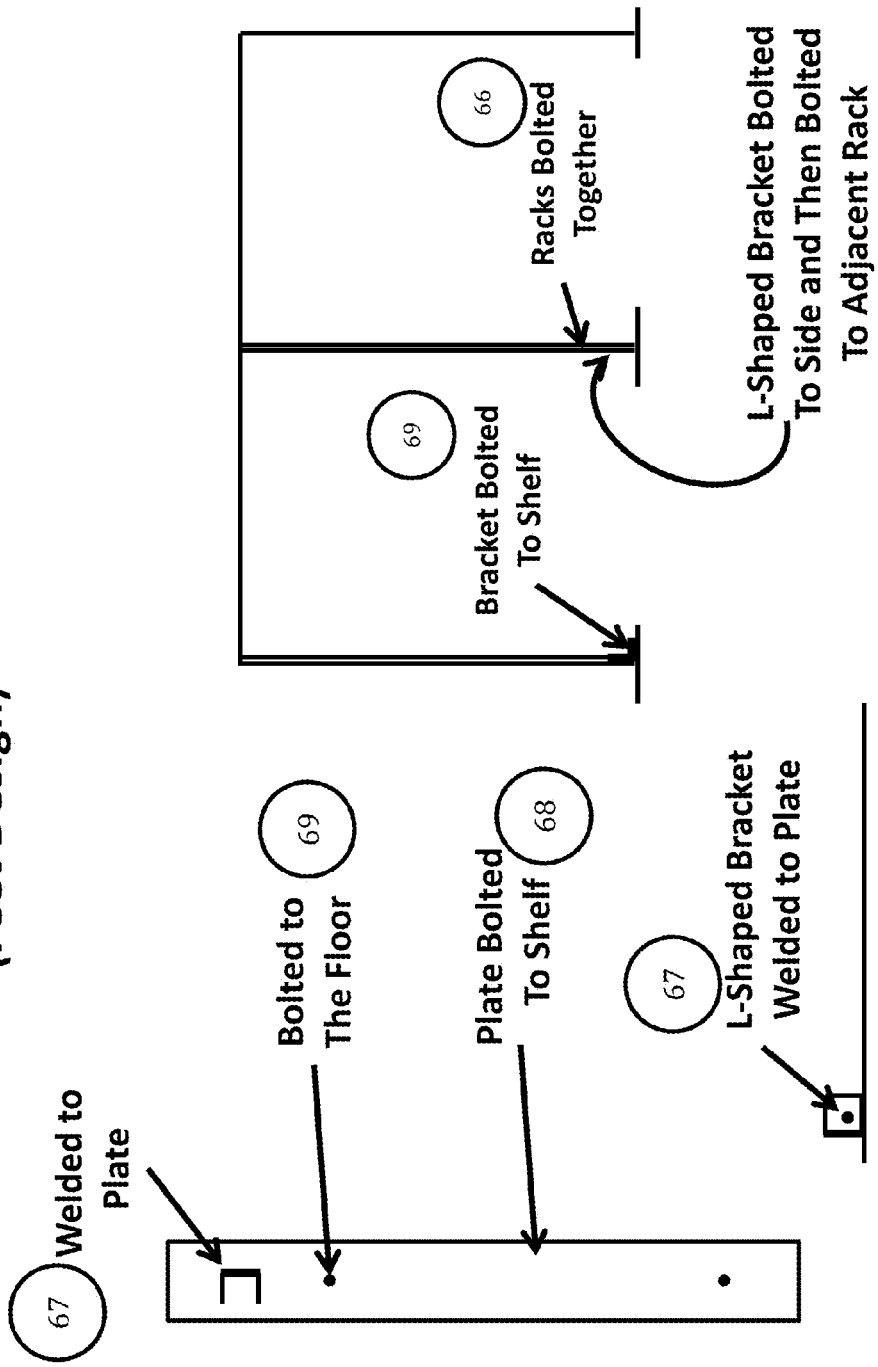
Figure 14 — Top View of the Rack System (Feet Design)

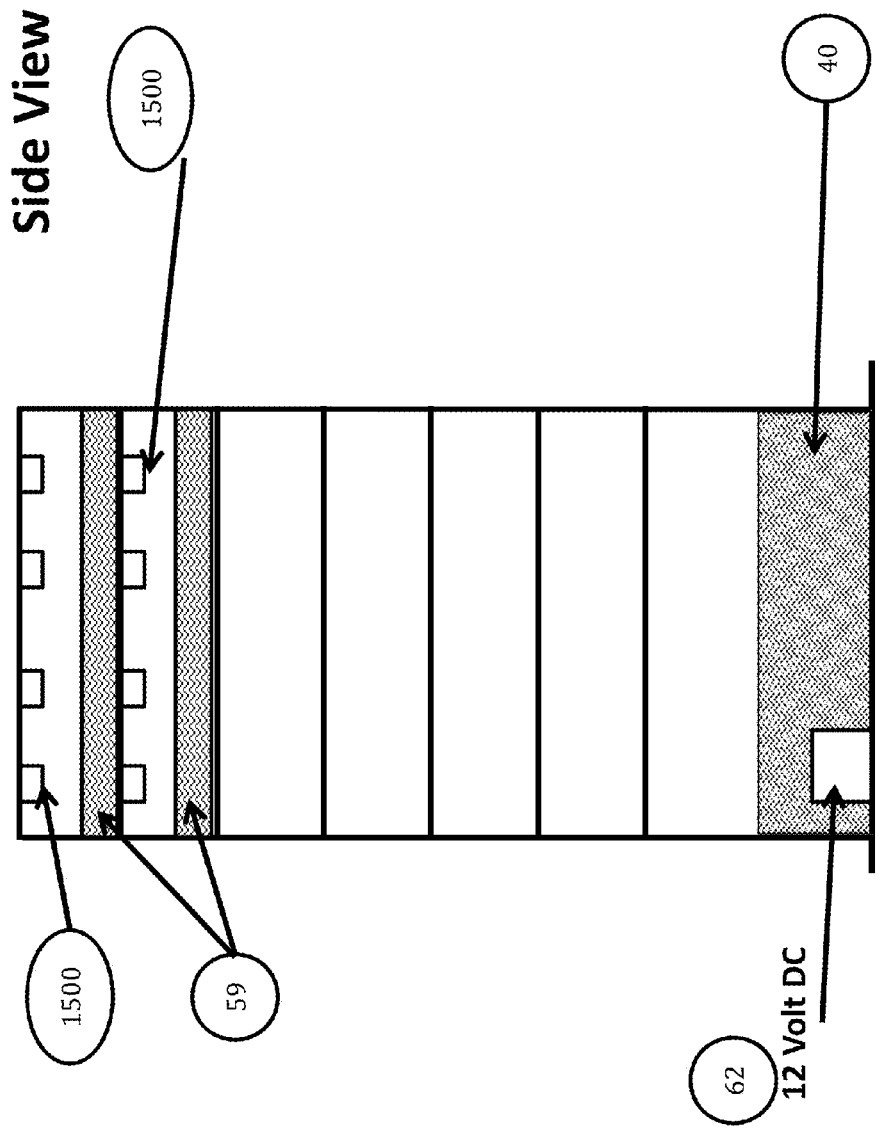

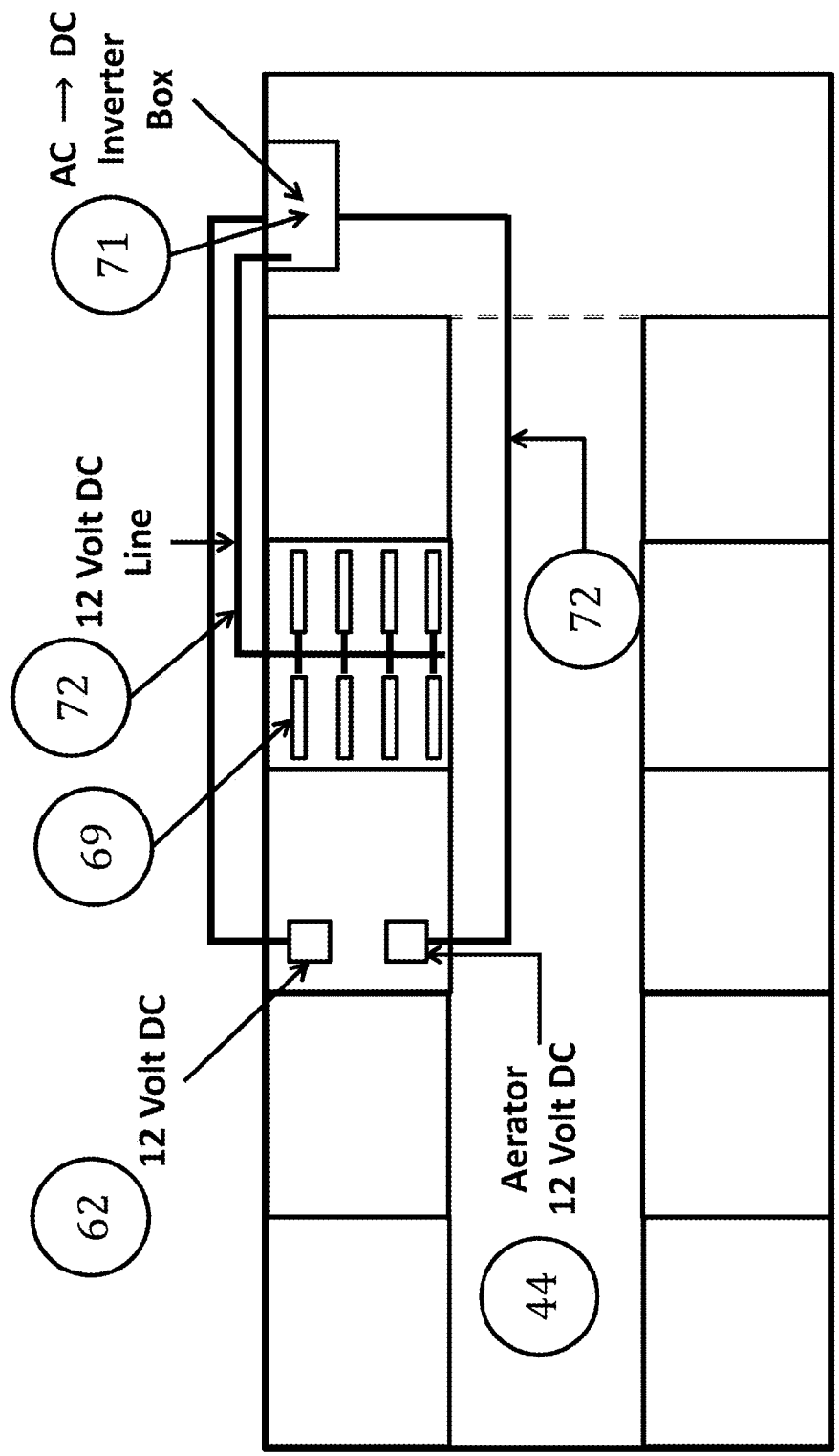

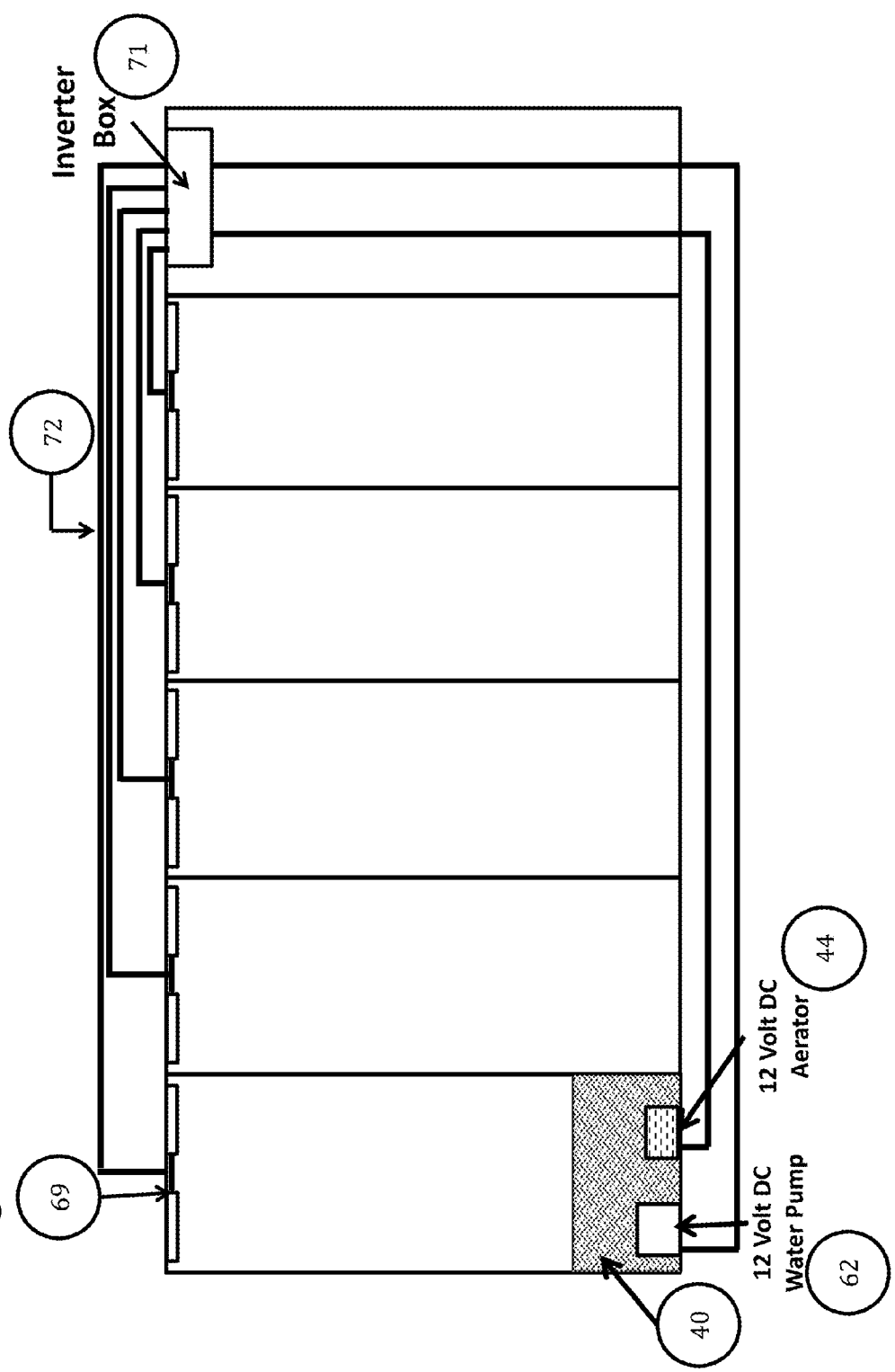

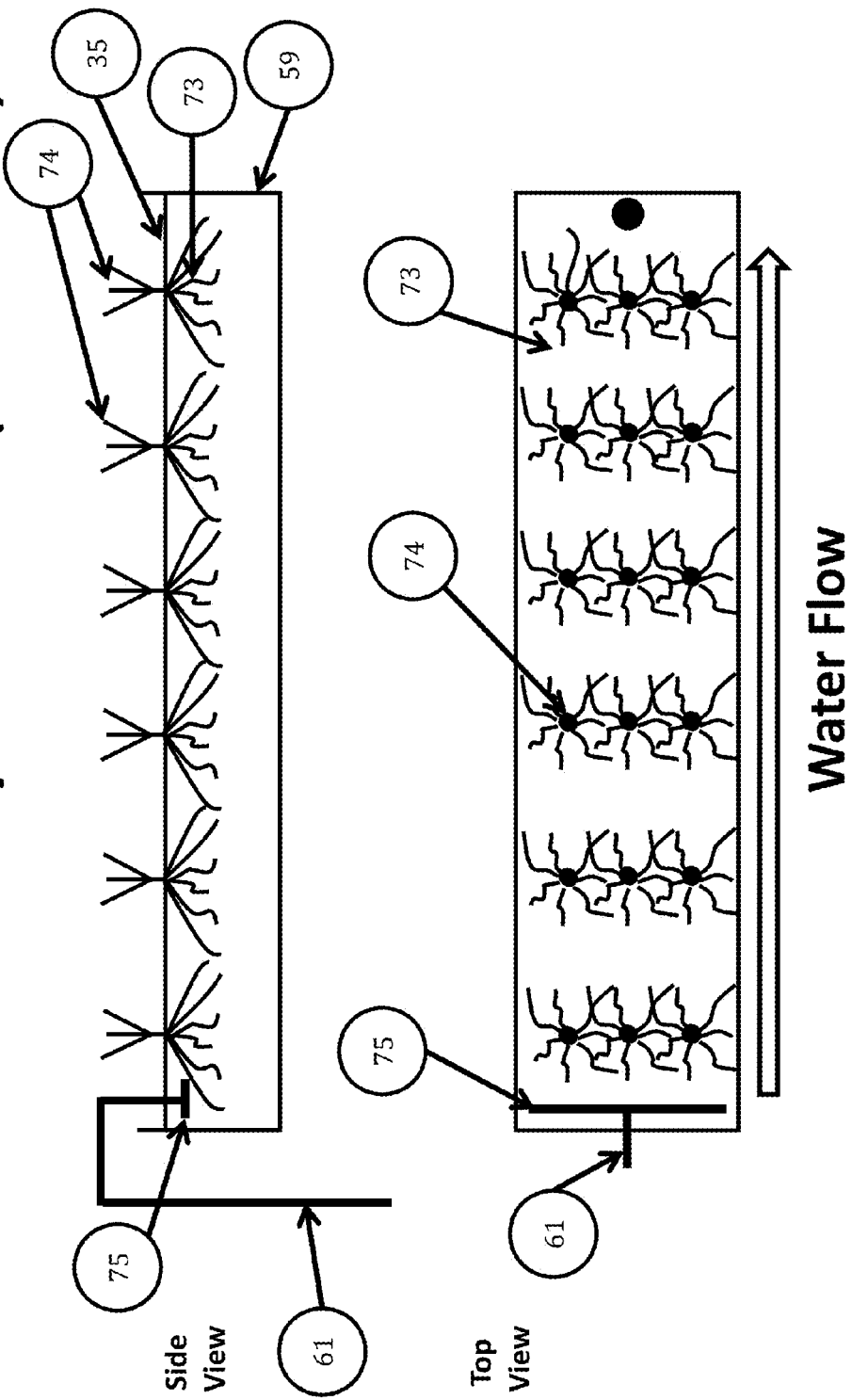
Figure 18  Method for Water Flow based On Root System Status (Full Growth)

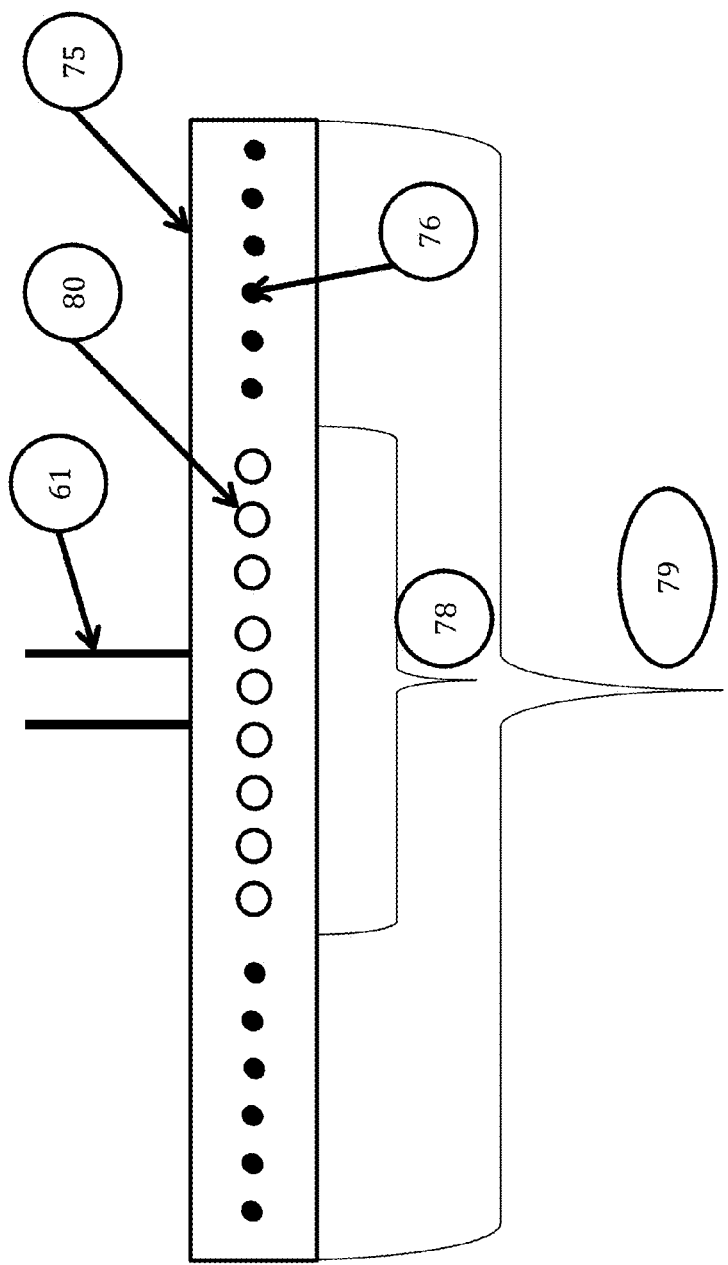
Figure 19 Apparatus for Dispersion of Water
79 → L = Total Length of dispersion bar
78 → ½ L
76 → S = Diameter of holes for n Fig. 20    Timing of pH in Plant Growth Cycle
           for Lettuce

(81) Phase $A_1$ => 1.2 * P

(82) Phase $A_2$ => 1.1 * P

(83) Phase $A_3$ => P

(84) Phase B  => 0.6 * P

(85) Phase C  => 1.2*P

(86) Phase D  => P

(87) P = Average Plant pH Preference

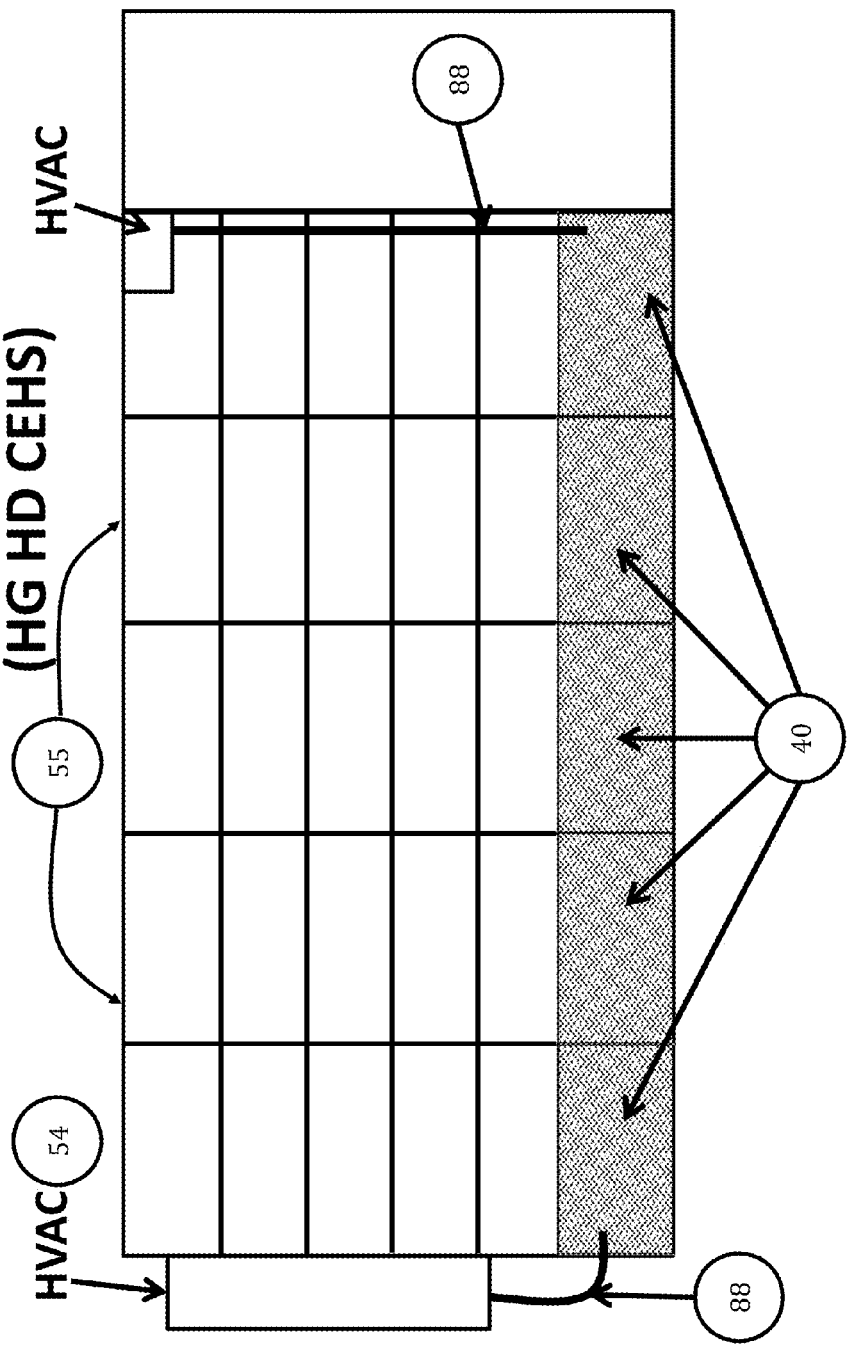
Figure 21 Water Recirculation & Dehumidification systems for reclaiming aspirated water in a (HG HD CEHS)

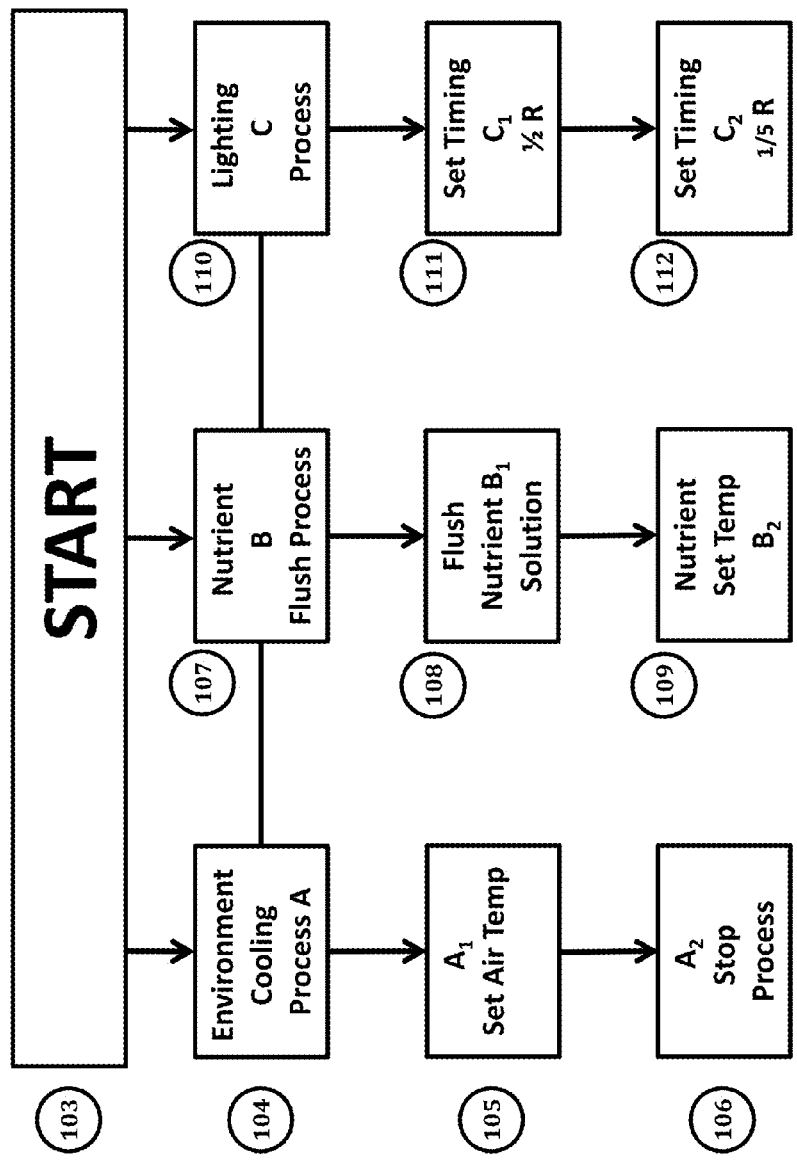
Figure 23    Cell Replication Control

Figure 24  Desired Cell Replication Control

| Appropriate Percentage of Reduced | |
|---|---|
| 0 – 10% | $A_1$ |
| 10% – 30% | $A_1, A_2, C_1$ |
| 30% – 45% | $A_1, B_2, C_1$ |
| 45% – 65% | $A_1, B_1, B_2, C_2$ |
| 65% – 80% | $A_1, B_1, B_2, C_2$ |

(113) (114) (115) (116) (117)

Figure 25  Cell Replication Control Variables (118) $A_1 \Rightarrow$ Air Temp < 64°F (119) $A_2 \Rightarrow$ Air Temp < 58°F (120) $B_1 \Rightarrow$ Change out nutrient solution for water with pH of 7

(121) $B_2 \Rightarrow$ Nutrient solution Temp < 64°F (122) $C_1 \Rightarrow$ 1/3 * R (123) $C_2 \Rightarrow$ 1/5 * R (124) R = Recommend Lighting Cycle for a given plant species in given hours/day.

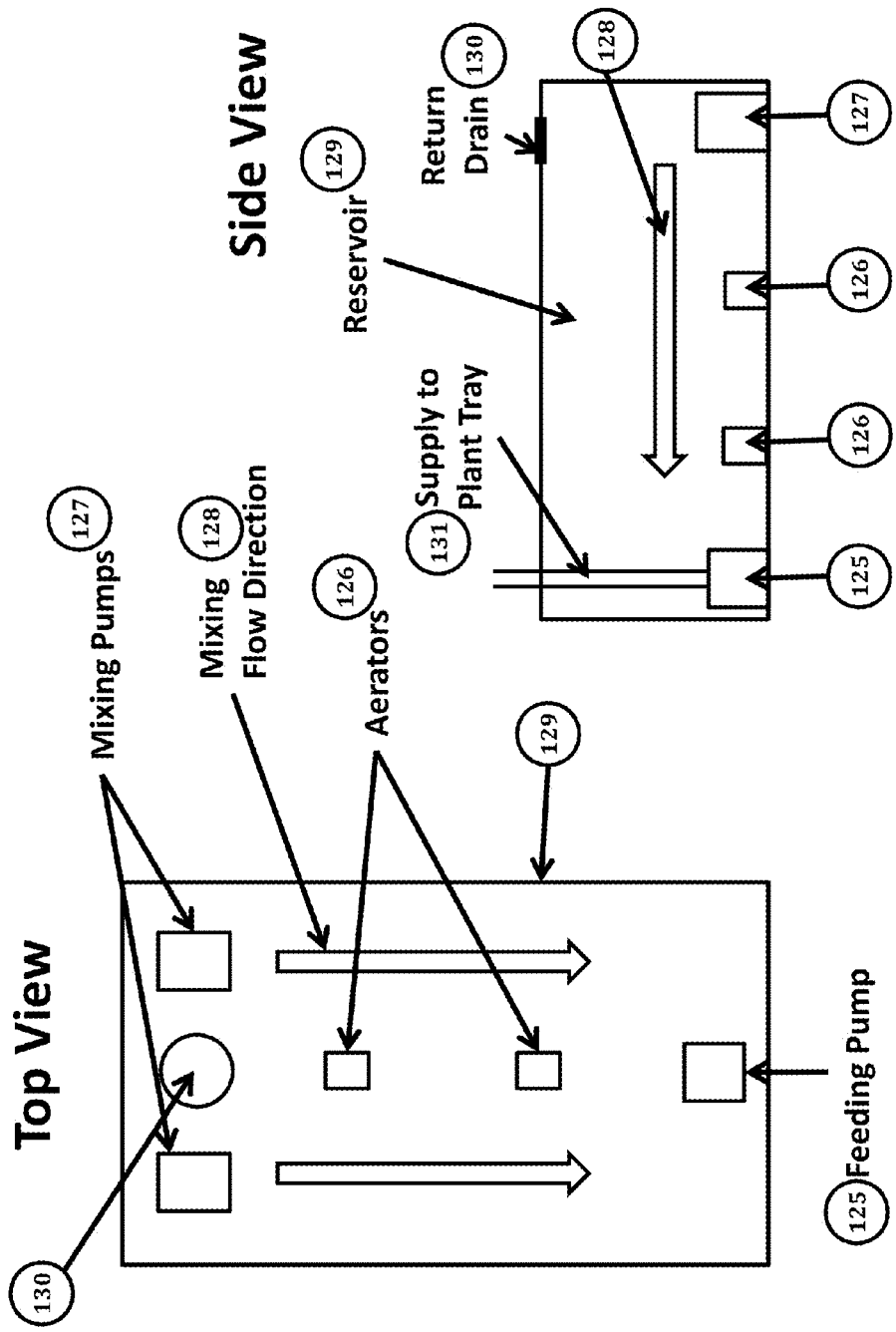
Figure 26 Nutrient Solution Mixing System

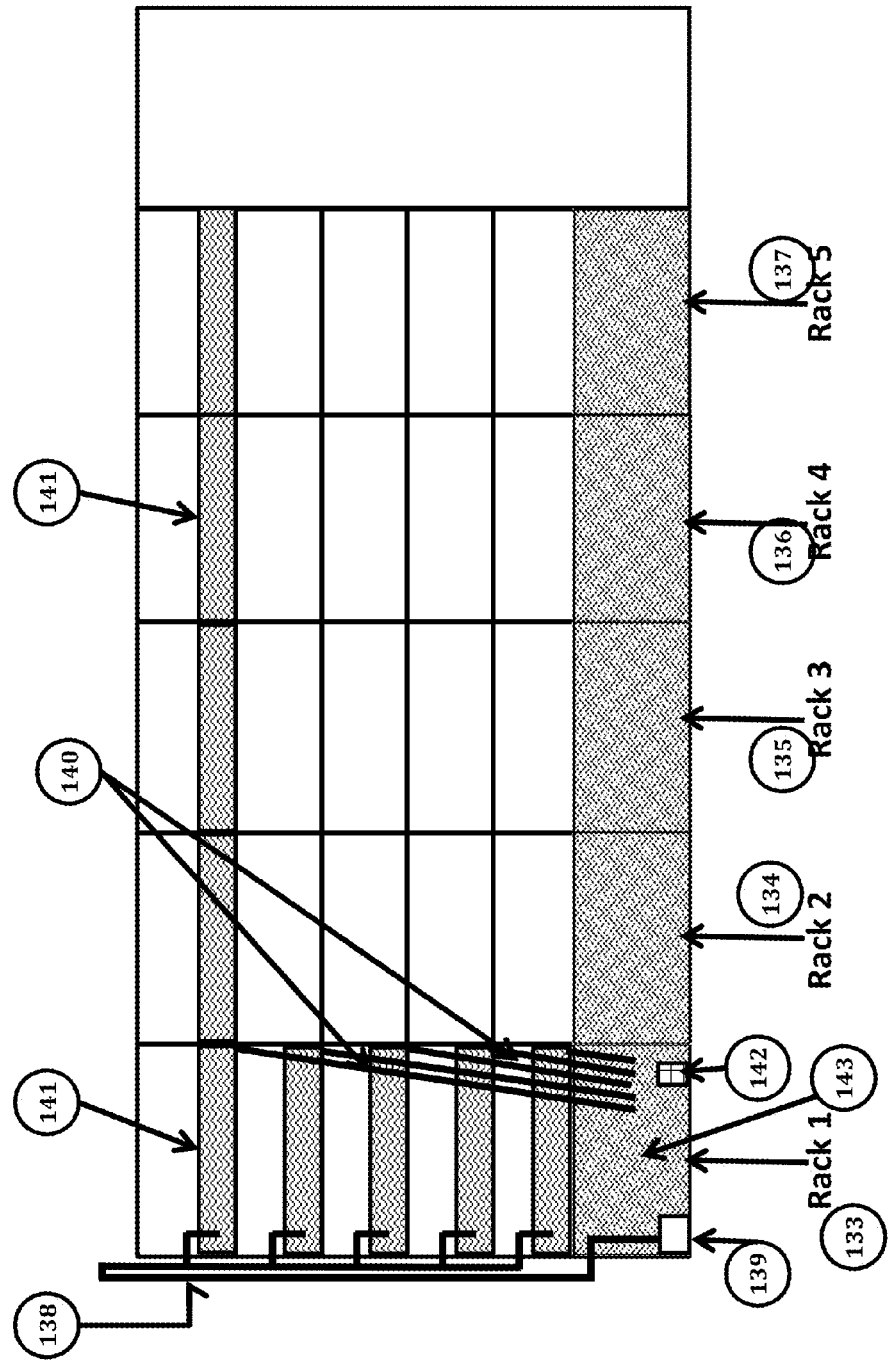
Figure 27  Distributed Hydroponic Solution Delivery System for Isolated Pathogenic Risk Mitigation Light Emitting Diode (LED)
Grow Light System in a high density hydroponic Environment

Figure 29

Light Emitting Diode (LED)
Red/Blue Lighting Configuration

Top View

```
R B R B R B R B R B
R R R R R R R R R R
R B R B R B R B R B
R R R R R R R R R R
```

$R_w$ = Wattage per Square Foot $R_w$ = 25 watts for Red/Blue LED
Red LED => 640Nm to 720Nm (81%)
Blue LED => 400Nm to 480Nm (19%)

LED LIGHT TIMING IN A HIGH GROWTH, HIGH DENSITY, CLOSED ENVIRONMENT SYSTEM

CROSS-REFERENCE TO RELATED APPLICATIONS

This application claims the benefit of the following provisional applications, each of which is hereby incorporated by reference in its entirety:

U.S. Provisional Application 61/784,837, filed Mar. 14, 2013.

BACKGROUND

Field

The disclosure herein relates to a high growth, high density, closed environment hydroponics system.

Discussion of Related Art

The cost of growing and providing vegetables and other produce to the population is increasing. The sprawl of the population takes more and more of the land available for conventional farming. The farms that exist are constantly being moved further away for the population centers. The increased distance of transporting the produce, and the increased cost of transportation overall causes increases in the produce costs to the consumer. The produce is also not as fresh as it once was since it has been transported increasingly longer distances.

The amount of land which supports conventional farming is shrinking. Therefore, there is a need to provide a new system for growing produce that can be implemented close to the population centers and also in areas that have not been able to be used for conventional farming.

SUMMARY

Disclosed herein is a high growth, high density, growing system and methods thereof. In an embodiment, the high growth, high density growing system is at least a partially closed environment. In an embodiment, the high growth, high density growing system is a closed environment. In an embodiment, the growing system is a high growth, high density, closed environment hydroponics system (HG HD CEHS). Throughout the specification, the high growth, high density, closed environment hydroponics system may be used as exemplary but any of the methods and systems described herein may be used with any growing system.

A method of accelerating plant cell growth in a growing system may include a combination of optimizing nutrient solution in accordance with a growth curve, calibrating the pH of the solution to optimize nutrient absorption throughout the growth curve, controlling temperature throughout the growth cycle and at maturation, adjusting the lighting in accordance with a growth stage, and controlling the delivery of carbon dioxide. The growing system may be a closed environment hydroponic system.

In an aspect, a method may include determining light timing to optimize plant growth, wherein determining utilizes an equation based upon the variables of a plant species, wherein the variables are: seedling stress time (SS), growth maturity height, plant maturity phase, and plant growth time. Growth start height may be measured for a seedling planted into the hydroponic system from the base of the growth medium to the top of the seedling plant. Growth maturity height may be measured from the base of the growth medium to the top of the fully mature plant.

In an aspect, a system for optimal carbon dioxide enrichment for plant production in a growing system may include a carbon dioxide tubing hung in a secured position on one side of a grow media tray to form a distribution point. The system evenly disperses carbon dioxide across the hydroponic grow media from the distribution point. A maximum amount of released carbon dioxide will be across the hydroponic grow media, thus allowing for the full potential of carbon dioxide enrichment within hydroponic system. The system forms a negative overhead pressure that forces expired oxygen to sink and be reclaimed into the hydroponic system. The expired oxygen may be recaptured in a water reservoir tank to improve nutrient oxygenation. The growing system may be a closed environment hydroponic system.

In an aspect, disclosed herein is a non-transitory computer-readable storage medium with an executable program stored thereon, wherein the program instructs a processor to perform the following steps: determine a plant growth profile, and supply carbon dioxide based on a plant growth profile.

In an aspect, a system for recapturing aspirated oxygen is via an aeration device that bubbles the oxygen into the hydroponic nutrient tank.

In an aspect, a system of electrically charging the nutrient reservoir in a growing environment to stimulate plant growth may include a liquid reservoir, and an electronically operated liquid-charging means for causing the liquid to be electrically charged in such a manner that the liquid charges the roots of the plant for stimulation. The liquid-charging means includes a protective overload device. The system may further include two power sources. The system may further include an isolator to protect against any electrocution. The system may further include an operating time means for recording the amount of time that the system has been in operation. The growing environment may be a closed environment hydroponic system.

In an aspect, a method of heating and cooling a hydroponic nutrient solution may be based an equation with variables related to a plant species, wherein the variables include seedling stress time—SS, growth maturity height, plant maturity phase, and plant growth time. Growth start height may be measured after the seedling is planted into the hydroponic system from the base of the growth medium to the top of the seedling plant. Growth maturity height may be measured from the base of the growth medium to the top of the full mature plant.

In an aspect, a method of growing plants may include placing plants in a receptacle and providing conditions for growth of the seedlings, and growth of the mature plants, and then removing the mature plants from the receptacle. An apparatus for growing plants may include a series of stacked shelves in a rack, each capable of receiving a receptacle containing seeds or plants, each divided into a number of successive zones in which the plants may be exposed to the necessary environmental conditions for the particular stage of growth in that zone. A receptacle for receiving plants may include a flood tray having a drain hole, the drain hole being fitted with a drain control means that includes a tube that returns to the reservoir. The series of racks may be connected together from left to right and a further series of racks may be connected from right to left. Shelving may be mounted one above the other, so that the headroom of the lower rack is measured at approximately a distance equal to the maturity height of the plant. A plurality of series of shelves are mounted one above the other, each series of shelves being provided with lighting means, water and/or nutrient feeding means, and drain means. The feeding means to each series of inclined racks may be divided up into zones along the length of the rack so that different feeding solutions can be dispensed to each zone. Each zone may have an associated drain system which may collect the drained feed solution individually or return it all to a common sump hole for disposal or recycling.

In an aspect, a low voltage growing system may include lighting and mechanical systems connected to a step down transformer that converts high voltage a.c. power to d.c. low voltage power. The entire high density hydroponic environment may be powered by a d.c. voltage system. The d.c. power may supply any of the system mechanicals. The growing system may be a closed environment hydroponic system.

In an aspect, a method of growing a plant may include supplying an even nutrient solution to the root of the plant across a hydroponic solution medium regardless of the grow medium used. The normal nutrient solution may be drained and a measured amount of more highly concentrated nutrient solution may be introduced into the nutrient supply. In embodiments, the nutrient solution passes only once across the root system, and the solution in the collecting area is drained. The nutrient solution conveyed to the collecting area is subsequently fed to said plant. The supply of nutrient solution is static. In an aspect, an apparatus for cultivating a plant hydroponically by the method may include a tube of numerous flow holes to distribute the nutrient solution over a higher density root system. The apparatus may further include a facility to adjust the flow holes according to the plant species and the level of root growth. The plant receives the same amount of nutrient solution in the center of a hydroponic flood tray as at the edges of the system. The collecting means may include a vessel floating in said supply of nutrient solution. The supply of nutrient solution is static. The method may be employed in a closed environment hydroponic system.

In an aspect, a method may include determining pH of a nutrient solution by an equation based upon the variables of a plant species. These variables are: seedling stress time—SS, growth maturity height, plant maturity phase, and plant growth time and the average plant pH preference. Growth start height may be measured from when the seedling is planted into the hydroponic system and from the base of the growth medium to the top of the seedling plant. Growth maturity height may be measured as the height at full maturity of the plant species In an aspect, a system may include a dehumidifier in a closed hydroponic environment of the kind having a vapor compression circuit containing an evaporator and a condenser and arranged to operate with alternating water extraction and defrost phases, the dehumidifier including a temperature sensor arranged to monitor the operating temperature of the evaporator, and a control facility for controlling the duration of the water extraction and defrost phases. The control facility may be arranged to read a reference temperature from the said sensor during a water extraction phase and starts the defrost phase when the evaporator temperature reaches a calculated temperature below the reference temperature. The control facility may be arranged to take temperature readings from the said sensor at predetermined intervals and calculate the rate of fall of the evaporator temperature, starting the defrost phase when the calculated rate of temperature fall exceeds a predetermined figure. The water extracted may be recirculated into the water reservoirs in the hydroponic container.

In an aspect, a method may include controlling certain environmental factors in a high density hydroponic environment to considerably slow down the plant cell replication process thereby extending the growing cycle of a given plant species. The air, lighting, and nutrient systems are controlled to adjust the growing cycle of a given plant species.

In an aspect, a method may include evenly mixing a hydroponic nutrient solution in a reservoir system based upon placing certain mixing pumps and aerators located to provide adequate mixing. The mixing pumps may create a failsafe design by mixing the solution even if one of the mixing pumps fails.

In an aspect, a system is disclosed whereby individual hydroponic shelving racks are arranged in a closed container environment and each rack has its own nutrient solution and tray assembly. The lighting, and nutrient systems for the independent hydroponic racking system are controlled such that there is no possibility of intermixing of lighting or nutrient solutions across racks.

In an aspect, a lighting unit system in a growing system may include at least one LED lighting source, wherein each lighting source includes a support structure, a plurality of light emitting elements along a length of said support such as a shelving unit, and a shelving unit from which the support is to be hung. The light system is designed to provide the maximum wattage of at least 15 watts per square foot of hydroponic coverage area. At least some of the light emitting elements emit light of a first color and at least some of the light emitting elements emit light of a second color. At least one lighting source may include at least one of a mechanical or electrical connection to another lighting strip. The lighting unit is configured to selectively provide at least one of indirect light distribution or direct light distribution. The lighting unit may further include a controller configured to vary a light output of the lighting unit. The support structure may be a rigid, elongated structure similar to a rack shelving unit. The growing system may be a closed environment hydroponic system.

In an aspect, a growing system for promoting the rapid growth of seedlings may include a substantially closed container, a nutrient solution within the closed container, a seedling positioned within the nutrient solution, a grow light, at least one sensor adapted to observe growth of the seedling, and a controller coupled to the grow light. The controller and the at least one sensor may be adapted to read information from the sensor to determine if growth has occurred, calculate a seedling stress duration, wherein the seedling stress duration commences with the positioning of the first seedling in the growing system and terminates when growth is observed in the first seedling, divide the seedling stress duration into a plurality of subphases, determine a subphase factor for a second seedling positioned in the growing system based on which subphase the second seedling has reached based on an elapsed time, calculate the total number of on/off light cycles and a duration for each on/off cycle, wherein one cycle is turning the lights on and off, and control the grow light to execute the total number of calculated on/off light cycles for the calculated duration of time the lights are on and time the lights are off during each cycle in the growing system. The subphase factor may be determined by multiplying the seeding stress duration by a fraction. The number of on/off light cycles is determined by dividing the total timing of the light cycle in the subphase by two times the subphase factor. A duration the lights are on and a duration the lights are off in each on/off cycle is calculated by multiplying the subphase factor by 60 minutes. There may be three subphases and the fraction for a first subphase is $1/600$. There may be three subphases and the fraction for a second subphase is $1/300$. There may be three subphases and the fraction for a third subphase is ¹/₂₀₀. The grow light may be at least one of a red LED light and a blue LED light. The grow light may be of a wavelength selected in accordance with a predetermined plant species. The growth may be observed by a visual analysis of the first seedling. The sensor to monitor growth of a plant may be one or more of a video observation, a laser sensor, and a location/proximity sensor. The growth of the first seedling may be determined by measurement of a weight of the first seedling. The sensor to monitor growth of a plant may be an $O_2$ sensor. The growth of the first seedling may be determined by measurement of consumption of a nutrient in the nutrient solution. The growing system may be a hydroponic growing system.

In an aspect, a method for accelerating growth of a seedling positioned in a nutrient solution in a growing system may include the steps of observing a seedling to monitor growth of the seedling over the course of a plurality of plant maturity phases, wherein a second plant maturity phase commences when growth is first observed in the seedling and terminates with the development of a full leaf or bud relative to the other leaves or buds in the seedling, a third plant maturity phase commences at the end of the second plant maturity phase and terminates when full plant maturity occurs in the plant as determined by the plant species, and a fourth plant maturity phase commences with reaching full maturity and terminates when the plant is ready to be harvested. The method may further include calculating a number of hours for an LED grow light to remain on during a first portion of the second plant maturity phase by multiplying a first fraction by a recommended lighting cycle in hours for a given plant species, calculating a number of hours for the LED grow light to remain off during the first portion of the second plant maturity phase by subtracting the first fraction times the recommended lighting cycle from twenty-four hours, calculating a number of hours for the LED grow light to remain on during a second portion of the second plant maturity phase by multiplying a second fraction by the recommended lighting cycle in hours, calculating a number of hours for the LED grow light to remain off during the second portion of the second plant maturity phase by subtracting the second fraction times the recommended lighting cycle from twenty-four hours, and executing the on/off light cycles for the calculated durations in the growing system by controlling a grow light in accordance with the on/off light cycles to result in accelerated growth of the seedling. The first fraction may be ⅓ and the second fraction may be ⅔. The method may further include using the recommended lighting cycle for a number of hours the LED grow light is to remain on per day during the third plant maturity phase and calculating a number of hours for the LED grow light to remain off during the third plant maturity phase by subtracting the recommended lighting cycle from twenty-four hours. The method may further include calculating a number of hours for the LED grow light to remain on per day during the fourth plant maturity phase by multiplying ½ times the recommended lighting cycle and calculating a number of hours for the LED grow light to remain off during the fourth plant maturity phase by subtracting ½ times the recommended lighting cycle from twenty-four hours. At least one of a grow light wavelength, temperature, and nutrient concentration may be varied over the plant maturity phases. The method may further include the step of withdrawing nutrient solution when the plant reaches the fourth plant maturity phase. The method may further include the step of terminating all light cycles when the plant reaches a harvest stage. The method may further include the step of reducing the temperature in the growing system when the plant reaches the fourth plant maturity phase. The grow light may be at least one of a red LED light and a blue LED light. The grow light may be of a wavelength selected in accordance with a specific plant species. Growth may be observed by a visual analysis of the seedling. Growth of the seedling may be determined by one or more of a video observation, a laser sensor, and a location/proximity sensor. Growth of the seedling may be determined by measurement of a weight of the seedling. Growth of the seedling may be determined by measurement of an $O_2$ output in the system by an $O_2$ sensor. Growth of the seedling may be determined by measurement of a concentration of a nutrient solution to determine the seedling consumption.

In an aspect, a growing system for promoting the rapid growth of seedlings may include a substantially closed container, a nutrient solution within the closed container, a seedling positioned within the nutrient solution, a grow light, and a controller coupled to the grow light adapted to receive information on a growth of the seedling, calculate a seedling stress duration, wherein the seedling stress duration commences with the positioning of the first seedling in the growing system and terminates when growth is observed in the first seedling, divide the seedling stress duration into a plurality of subphases, determine a subphase factor for a second seedling positioned in the growing system based on which subphase the second seedling has reached based on an elapsed time, calculate the total number of on/off light cycles and a duration for each on/off cycle, wherein one cycle is turning the lights on and off, and control the grow light to execute the total number of calculated on/off light cycles for the calculated duration of time the lights are on and time the lights are off during each cycle in the growing system. The growing system may be a closed environment hydroponic system.

These and other systems, methods, objects, features, and advantages of the present disclosure will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The disclosure and the following detailed description of certain embodiments thereof may be understood by reference to the following figures:

FIG. 2 describes the variables used to compute a timed growth curve for a specific plant species.

FIG. 6 is a side view of the system.

FIG. 7 is a top perspective view of the system.

FIG. 10 describes the optimum temperature range for a plant which has a recommended hydroponic nutrient temperature range of "R" for a given plant species.

FIG. 11 is a top view of a rack apparatus with structural bracing plate connecting the racks together.

FIG. 12 is a diagrammatic indication of an individual rack that describes the nutrient supply and drainage system for the apparatus of FIG. 11.

FIG. 13 is a plan view of a rack system from a vertical view detailing the brace system.

FIG. 14 is a descriptive view of the rack feet design and its installation to the floor or the hydroponic system.

FIG. 15 depicts a side view of the lighting and pump elements of a hydroponic system using a low voltage d.c. system.

FIG. 16 depicts a top view of the wiring design of a 12 volt d.c. system and the placement of the inverter box.

FIG. 17 depicts a side view of the wiring design of the hydroponic growing system.

FIG. 18 depicts a top and side view of a flood tray and the nutrient flow from the entry point into the flood tray to its drain.

FIG. 19 depicts an apparatus to insert in the flood tray to produce an even distribution in a mature root environment.

FIG. 20 describes the different phases of plant growth and the optimal pH level based upon the stage of growth.

FIG. 21 depicts a dehumidification system.

FIG. 23 describes a flow chart system to determine which variables to control in chronological order.

FIG. 24 illustrates a table of variables to control that correspond to the desired reduction in plant cell growth.

FIG. 25 illustrates environmental variables used in the hydroponic environment to control the plant cell replication.

FIG. 26 depicts a system for nutrient mixing.

FIG. 27 is a side view of a hydroponic container consisting of a number of hydroponic shelving racks.

FIG. 29 outlines the required wattage per square foot and the placement of LED lights.

DETAILED DESCRIPTION

Figure 1A:
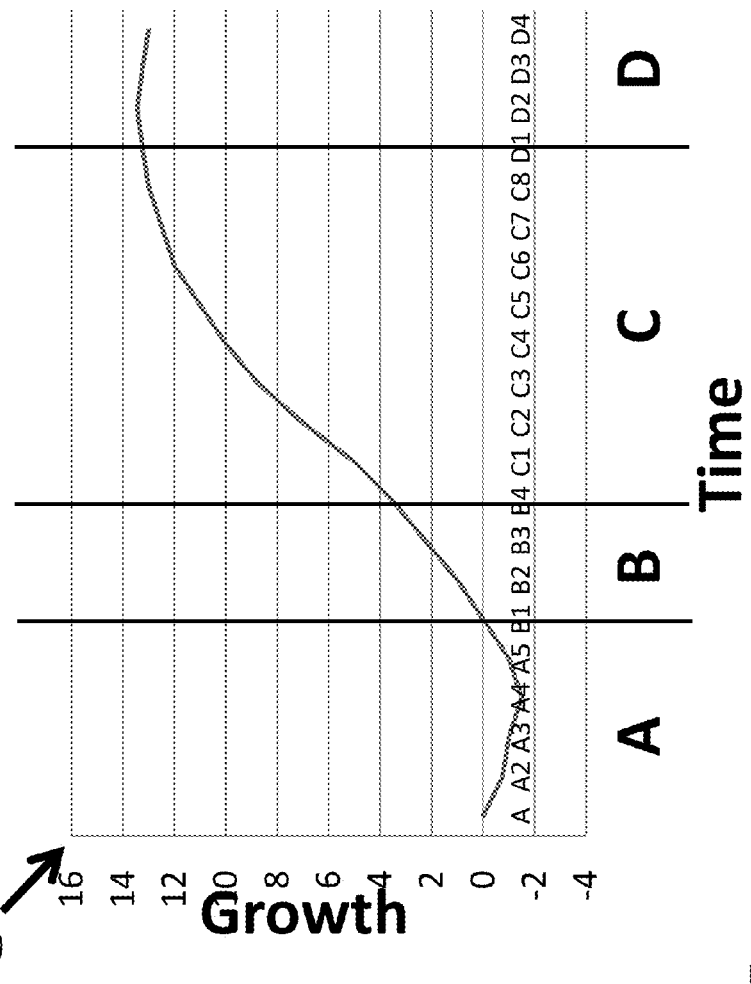
FIG. 1A describes a general plant growth curve including different phases of plant development.

In an aspect, a high growth, high density, closed environment hydroponic system for growth of plants on a continuous basis is described. The system features very rapid growth and high, pesticide-free, on-site production with a low carbon footprint. The system enables multiple harvests from the same seedling between retooling. The system enables the production of produce that has never been touched or sprayed and exhibits a long shelf life. In embodiments, various methods and systems disclosed herein may be used individually in a growing system. In embodiments, one or more methods and systems may be used in combination with one another in a growing system. Further, various methods and systems disclosed herein may be used in any growing system including hydroponic systems, aquaculture systems, aeroponic systems, soilless systems, terrestrial systems, and the like.

In an aspect, a method for adjusting the timing of an LED lighting system of a high-density growing system is provided. The growing system may be a closed environment hydroponic system. The timing of the lighting system is calculated from an equation based upon the seedling growth inside the hydroponic environment along with the power and distance of the LED grow lighting. The ON and OFF timing of the LED lights is directly correlated to the plant's relative progress on the standard plant growth curve. Represented by an equation, the timing of the lights may be determined by a number of variables along the plant growth curve to optimize the total time from which plants are grown from a first stage to a second stage.

LED light timing is an important aspect of plant growth in a hydroponic environment. LED lighting, which may include lights in the red and blue spectrum, may play a role in the plant's photosynthetic reaction. Grow lighting provides the energy that drives the photosynthetic reaction in the chloroplast, thus, the timing of plant exposure to this energy source is important in order to coordinate the photosynthetic reaction with the building and replication of plant cells. Optimizing the photosynthetic reaction in a plant is important. If too little energy (i.e. too little light) is provided, not enough of the photosynthetic reaction may occur to provide the sugar needed for cell replication. If too much energy (i.e. too much light) is provided, energy that is not used in photosynthesis is transferred as heat into the plant cells, which can damage or destroy the cells. Therefore, an equation may be used to determine the optimum growing cycle for the plant regardless of the plant species. The present disclosure provides a method for optimizing crop production in a growing system by using a timed lighting algorithm.

Various plant maturity phases and other variables may be described herein. Plant maturity phase—A is determined from the time the plant is positioned in the hydroponic system until the first growth occurs in the plant. Plant maturity phase—B is determined from the time the plant starts growing until new growth which could be either leaves or buds occur. Plant maturity phase—C is determined from the time of new leaves or buds until the time plant maturity occurs in the plant as determined by the plant species. Plant maturity phase—D is determined at the time the plant is ready to be harvested.

Unless stated otherwise, "SS" refers to the total seedling stress time measured in the total number of hours from the time a plant seedling is planted in the hydroponic grow system 34 until the time growth is noticed in the seedling itself. Growth may be noted by a visual analysis but may also be noted by video observation, laser sensors, or location/proximity sensors. Automatic size/growth stage measurement may be made by examining the height, such as by video or laser or the like, weight of the plant, $O_2$ sensor to measure $O_2$ output in the air, PPM concentration of the nutrient solution to determine consumption (e.g. as plants consume more water, elementals get more concentrated), and the like.

Unless stated otherwise, "$A_i$" refers to the ratio factor, also known herein as a subphase factor, used when turning on and off the lights in the plant growing environment. Unless stated otherwise, "$AT_i$" refers to the total number of minutes the grow lights remain ON and an identical number of minutes the grow lights remain OFF. Unless stated otherwise, "$T_s$" refers to the total time in a given Phase $A_i$ measured in hours. Unless stated otherwise, "$C_s$" refers to the total number of lighting cycles in a given Phase $A_i$ (that is, a complete ON and OFF operation of equal time period AT$_t$). Unless stated otherwise, "R" refers to the daily recommended lighting time for a given plant species measured in hours.

Figure 1B:
FIG. 1B depicts a graph of seedling stress.
Figure 3:
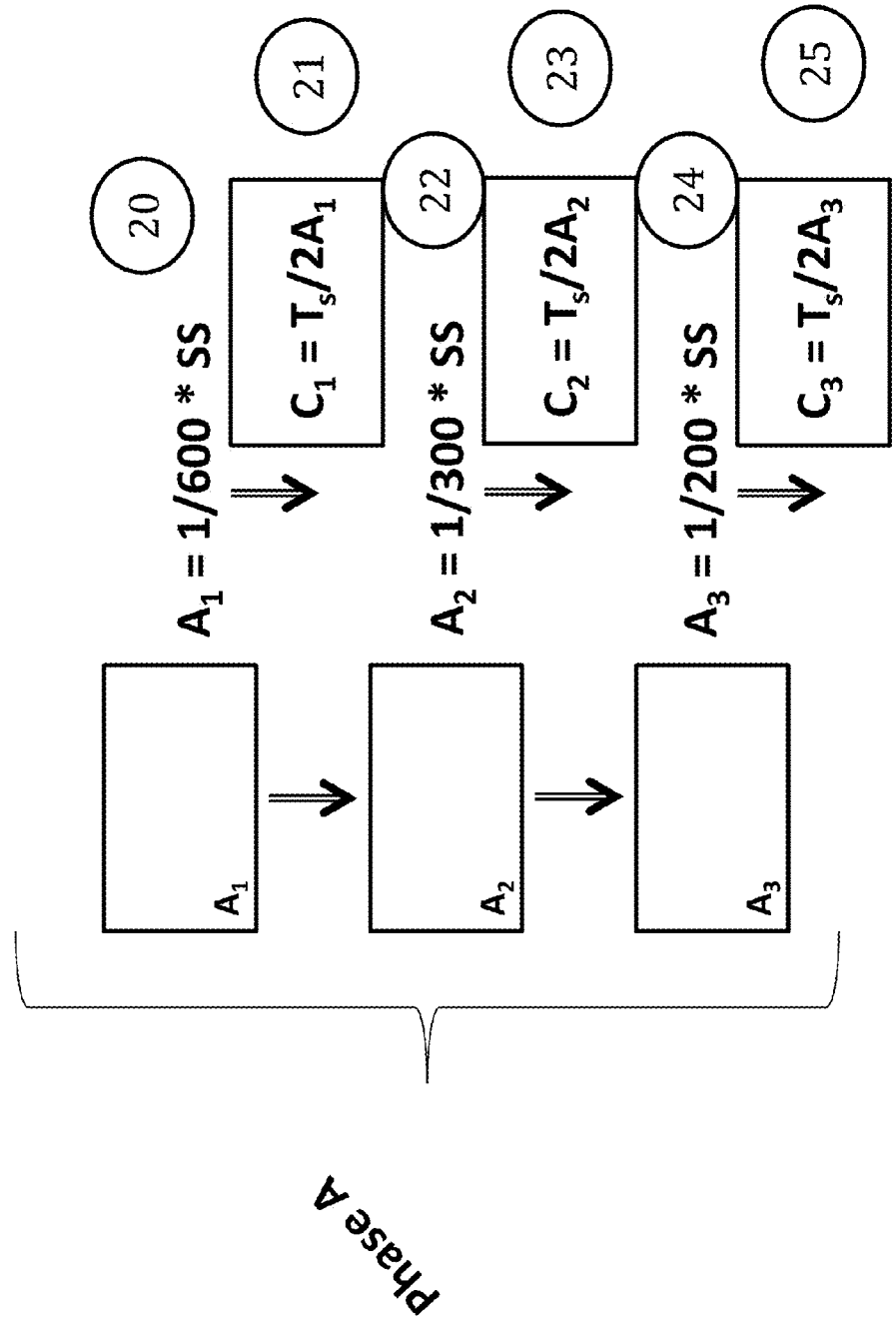
FIG. 3 describes the formulas used for Phase A in the cycle of growth of the plant.

Referring to FIGS. 1A and 3, the plant growth curve is divided among four distinct phases of growth, Phases A, B, C, and D, which have been previously described herein. Phase A is the seedling stress phase whereby seedlings are immersed in a growth medium and begin to die before the roots have the ability to take in nutrients. Data in FIG. 1B illustrates that Phase A may be further delineated into three different subphases of seedling stress growth. These three subphases of seedling stress growth may be equal in timing. In one embodiment, a seedling stress phase duration may be 72 hours.

FIG. 3 delineates the three subphases labeled Phase A1, A2, and A3.

For Phase A1, determining the ratio factor of the seedling is done by multiplying the seedling stress time by 1/600, as in equation 20 depicted in FIG. 3. To determine the total number of ON/OFF cycles in this subphase, the total timing of the light cycle in Phase A1 is divided by two times the ratio factor of turning ON/OFF the lights, as in equation 21 depicted in FIG. 3. The timing intervals of these ON/OFF cycles is computed by taking the ratio factor of the seedling and multiplying it by 60 to determine the total number of minutes in the ON/OFF cycle, as shown in equation 14 depicted in FIG. 2.

For Phase A2, determining the ratio factor of the seedling is done by multiplying the seedling stress time by 1/300, as in equation 22 depicted in FIG. 3. To determine the total number of ON/OFF cycles in this subphase, the total timing of the light cycle in Phase A2 is divided by two times the ratio factor of turning ON/OFF the lights, as in equation 23 depicted in FIG. 3. The timing intervals of these ON/OFF cycles is computed by taking the ratio factor of the seedling and multiplying it by 60 to determine the total number of minutes in the ON/OFF cycle, as shown in equation 14 depicted in FIG. 2.

For Phase A3, determining the ratio factor of the seedling is done by multiplying the seedling stress time by 1/200, as in Equation 24 depicted in FIG. 3. To determine the total number of ON/OFF cycles in this subphase, the total timing of the light cycle in Phase A3 is divided by two times the ratio factor of turning ON/OFF the lights, as shown in equation 25 depicted in FIG. 3. The timing intervals of these ON/OFF cycles is computed by taking the ratio factor of the seedling and multiplying it by 60 to determine the total number of minutes in the ON/OFF cycle, as shown in equation 14 depicted in FIG. 2.

Once new leaves or buds have grown on the plant, the plant enters Phase B of the growth cycle. This phase is defined from when new growth is started until a full leaf or bud has developed relative to the other leaves or buds in the seedling.

Figure 4:
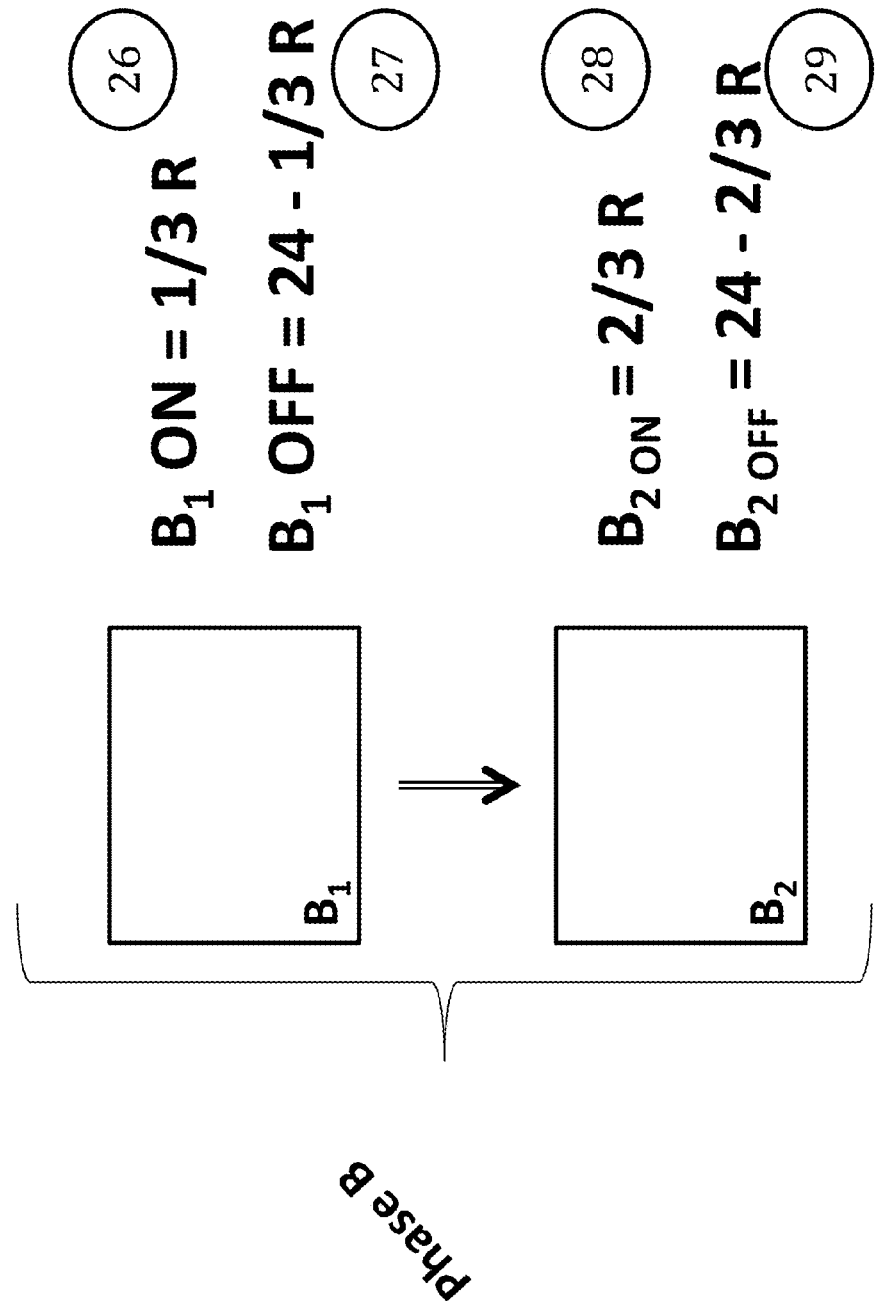
FIG. 4 describes the formulas used for Phase B in the growth cycle of the plant.

FIG. 4 illustrates the two subphases of Phase B labeled B1 and B2. In an embodiment, Phase B1 and Phase B2 may be equal in duration.

For Phase B1, the amount of hours ON for the lighting is determined by multiplying 1/3 by the recommended lighting cycle for a given plant species specified in hours, as shown in equation 26 depicted in FIG. 4. The OFF time is calculated by subtracting 1/3 times the recommended lighting cycle from twenty-four hours, as shown in equation 27 depicted in FIG. 4. In an embodiment, a recommended lighting cycle may be 18 hours.

For Phase B2, the amount of hours ON for the lighting is determined by multiplying 2/3 by the recommended lighting cycle for a given plant species specified in hours, as shown in equation 28 depicted in FIG. 4. The OFF time is calculated by subtracting 2/3 times the recommended lighting cycle from twenty-four hours, as shown in equation 29 depicted in FIG. 4.

Figure 5:
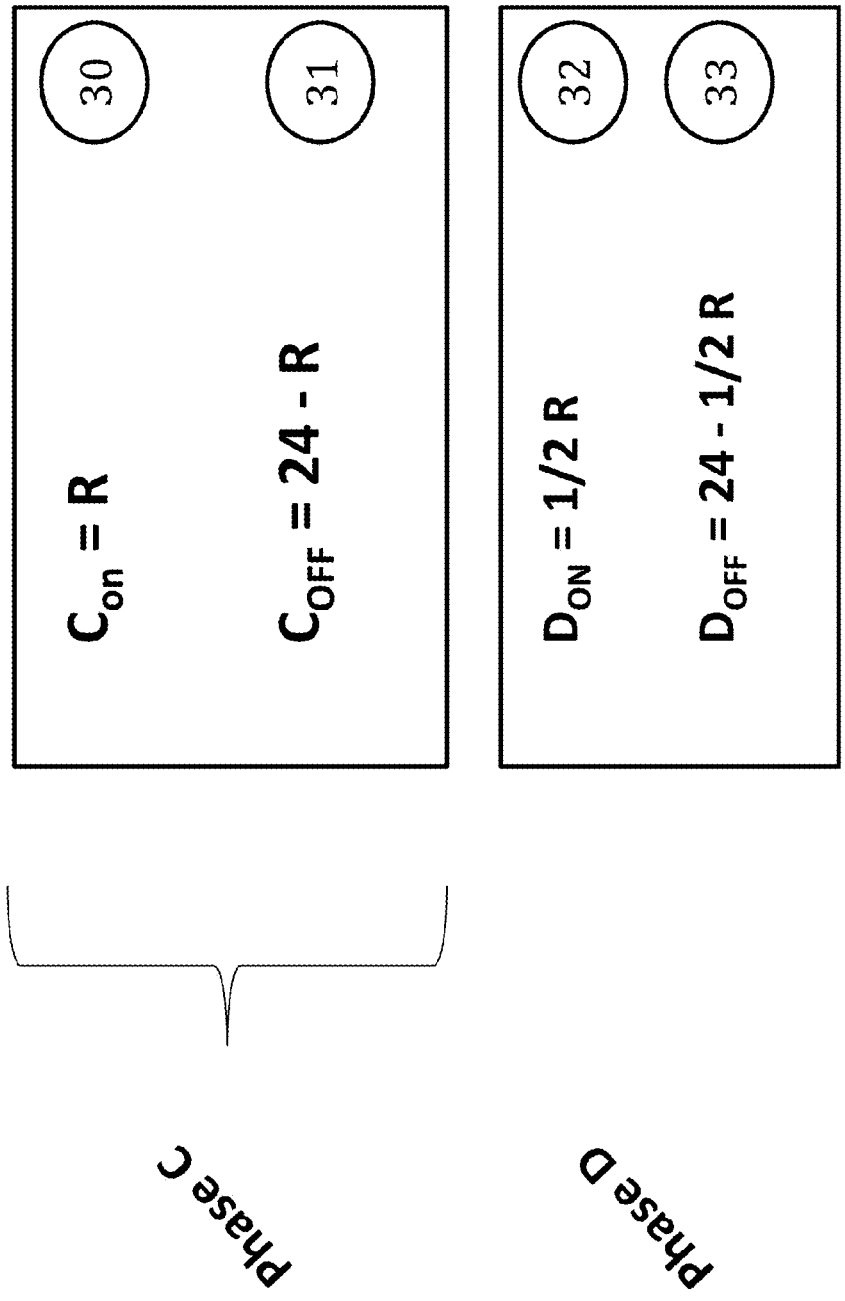
FIG. 5 describes the formulas used for Phases C and D in the growth cycle of the plant.

Referring now to FIG. 5, Phase C is considered the growth of a full leaf or bud relative to the previously determined plant's maturity. To calculate the timing of the lights, it is determined that the lights are in the ON position for a period that is recommended for that given plant species, as shown in equation 30. The time that the lights are OFF in this cycle is determined by subtracting the recommended light cycle in a given day from twenty-four to determine the hours OFF, as shown in equation 31.

For Phase D, also shown in FIG. 5, when the plant has reached its final maturity status, the time that the lights are ON is determined by multiplying 1/2 by the recommended lighting cycle, as shown in equation 32. The time the lights remain off is determined by subtracting 1/2 times the recommended lighting cycle from twenty-four hours.

In practice, exposing seedlings according to formula-driven light cycles may result in minimizing over-exposure to light energy in the early, sensitive stages of growth. One result may be a lighting profile such as seedlings receiving 1 hour of light exposure then 15 minutes rest initially, then 2 hrs on and 1/2 hr off, until the seedling is ready for a full light cycle, such as an 18 hr light cycle or 12 hrs on/3 hrs off.

In embodiments, the lighting system in the growing system may be programmed with a lighting algorithm in accordance with the formulas presented herein. Thus, a computer may be programmed to adjust the timing and duration of lights based on the identified stage of growth of a plant in accordance with calculated light cycles. Further, lights in the red and blue visible spectrum promote photosynthesis, so a computer may be programmed to utilize a mix of red and blue lighting, such as 75/25 red to blue, 85/15 red to blue, and the like. The red/blue mix may be programmed in accordance with a specific plant species. The algorithm may also be programmed to cause the LED or OLED lights to emit light of only a certain wavelength. The algorithm may be further programmed to select specific wavelengths in accordance with certain plant species. For example, basil has a photosynthetic preference for blue light and wavelengths of 430-660 nm. In an embodiment, plant-specific LED grow lights may emit light of a certain wavelength or color. Choosing plant-specific wavelengths/colors may optimize growth but may also enable minimizing power consumption by the hydroponic unit.

To prevent damaging mature plants and causing bitterness, light energy may be withdrawn when the plant approaches maturity/harvest stage and exposure to the nutrient solution should also be minimized. Concomitantly, temperature may also be reduced. Reducing lighting and heating in the pre-harvest stage may slow cell replication and may avoid excessive nutrient density.

In embodiments, one or more of the following may be varied based upon the maturity of the plant: light intensity, light spectrum applied, temperature, nutrition, $CO_2$ partial pressure/atmosphere mix, and humidity. In one embodiment, the nutrition provided is adjusted based upon root temperature. In other embodiments, the root temperature is adjusted based upon the nutrition provided. In an embodiment, the $CO_2$ pressure may be changed based upon the maturity of the plant. Other similar permutations of the interplay between variables may be envisioned.

This disclosure also provides a method and system for optimal carbon dioxide enrichment and the use of the oxygen generated by a plant for plant production. The system involves suspending carbon dioxide tubing in a secured position on one side of a plant media tray. The carbon dioxide tubing may also be secured to either the wall, the shelving unit, float tray or tub to enable blowing the carbon dioxide across the plants and allowing for the carbon dioxide to be evenly dispersed relative to the plants. The systems and methods for carbon dioxide enrichment may be used in any growing system, such as a closed environment hydroponic system.

When carbon dioxide levels are between 1000 and 1500 PPM, plants consume more light energy, base nutrients, water and oxygen to create a maximum rate of photosynthetic activity. This maximum rate of photosynthetic activity results in the astonishing plant yields gardeners strive for. The major hurdle in achieving this goal is the fact that the average level of carbon dioxide in the air is merely 300 PPM. Plants are composed of 80-90% carbon and water, while most of the carbon in plants comes from the minimal 300 PPM level of carbon dioxide in the air. While the indoor gardening industry has experienced amazing advances in lighting, nutrients, pest control, cloning and hydroponics, a limiting factor in maximizing the potential of an indoor garden is the amount (and lack of) available carbon dioxide in a grow room's climate.

Carbon dioxide is one of the three main components needed for plant growth, but the level of carbon dioxide in the air is only 0.03%. This compares to 78% Nitrogen, 21% Oxygen and 0.97% trace gases in normal air.

At such a low level of 300 PPM in the air, plants can easily consume all of the carbon dioxide in a hydroponic environment in a matter of hours. Plants are only able to produce up to the limited amount of carbon dioxide available, and once carbon dioxide levels are 200 PPM or lower, photosynthetic activity will diminish and may eventually stop altogether.

When the carbon dioxide supply in a hydroponic environment ceases to exist, so does photosynthesis. The process of photosynthesis mixes carbon dioxide and water to produce sugars and free oxygen. Photosynthesis occurs only in the presence of light and is therefore useless, and even harmful to enrich the plants with carbon dioxide during the dark (lights off) period of plant production.

Research has shown that increasing carbon dioxide will increase plant size, yield, vigor and speed up growth. Plants grown with increased levels of carbon dioxide are also less prone to common insect and disease issues. By increasing carbon dioxide levels to 1000-1600 PPM during the lights on period, research has shown carbon dioxide enrichment can increase yields 25-50%. However, a carbon dioxide concentration greater than 1600 PPM may cause partial or complete closure of the plant stomas (tiny openings in the plant leaf), which is a vital component for photosynthesis. Thus, careful control of ambient carbon dioxide levels is critical in maintaining an optimal grown environment.

Carbon dioxide is heavier than air. At 77 degrees Fahrenheit, carbon dioxide weighs 66 ounces per 3 cubic feet, while air weighs 42 ounces per 3 cubic feet at the same temperature. Aside from being heavier than air, carbon dioxide moves slowly downward from its distribution point and only travels a short distance through the diffusion process.

When implementing carbon dioxide enrichment methods, careful planning and positioning of equipment may ensure the dispersed carbon dioxide is directed toward the plant zone so it can be absorbed by the plants at a maximum capacity. Plants will consume all of the available carbon dioxide around their leaves within minutes. Thus, a need exists for a method and system that disperses carbon dioxide from an optimal distribution point, in a controlled manner to ensure optimal levels of carbon dioxide in the atmosphere, and in accordance with a lighting profile.

While there are different forms of carbon dioxide enrichment such as dry ice, fermentation and decomposition of organic matter, the two most commonly used forms of carbon dioxide enrichment are combustion generators and compressed carbon dioxide tanks.

Carbon dioxide generators are industrial units that burn fuel to produce carbon dioxide. As a result of the high amount of excess heat put out by these units, they are typically suggested for indoor gardens or greenhouse operations larger than 1000 cubic feet. To avoid the increased temperature issues that coincide with carbon dioxide generators, many closed loop hydroponic environments use a compressed carbon dioxide tank and regulator as their form of carbon dioxide enrichment.

Compressed carbon dioxide comes in metal containers under high pressure with pressure ranges from 1600 pounds per square inch (PSI) to 2200 PSI. This form of enrichment is referred to as a "timed release" system that releases a certain amount of compressed carbon dioxide from a tank at a timed rate of release. A "timed release" system requires a compressed carbon dioxide tank (20, 50 lb., or the like), tank regulator and a timer. The regulator controls the quantity of carbon dioxide emitted into the indoor garden atmosphere, while the timer controls precisely when and for how long the carbon dioxide is released.

Tubing, such as vinyl tubing, is attached to the tank regulator and positioned in the carbon dioxide distribution tube for dispersing the carbon dioxide. This tubing is referred to as "drilled" carbon dioxide tubing, where the carbon dioxide is vaporized through small holes in the tubing and homogenously dispersed throughout the hydroponic system.

Since oxygen is released by plants while carbon dioxide is being absorbed, this creates a dilution effect that diminishes the carbon dioxide concentration. As a result, it would be an improvement to have a method and system that would arrange the carbon dioxide tubing distribution point in a manner where the carbon dioxide would be absorbed while the expired oxygen is moved away from the plant. The removal of the expired oxygen from the system is important since it could migrate back into the plants and dilute the carbon dioxide concentrations. Thus, there is also a need of not only removing the oxygen from the vicinity of the plants but also capturing it, such as for utilization.

As a result, there is a need for a method and system that would evenly disperse carbon dioxide from a distribution point directly from the side of a grow area, regardless of the design and layout of the hydroponic system and capture the oxygen so that it could be utilized inside the nutrient tank of the hydroponic system.

FIG. 6 shows a side view of a system from which the carbon dioxide is distributed from the carbon dioxide tube and blown across the plants, as shown by vector 36. Carbon dioxide distribution in accordance with vector 36 results in a negative pressure zone above the plants by creating a circular wind motion 37 above the seedlings and plants. This forces the oxygen expired from the plants to roll over the hydroponic float media 35 and/or float tray downwards 38 towards the floor.

FIG. 7 depicts a top view of the system to distribute carbon dioxide across the plants. The carbon dioxide is exchanged with oxygen which is removed via inertial displacement.

Figure 8:
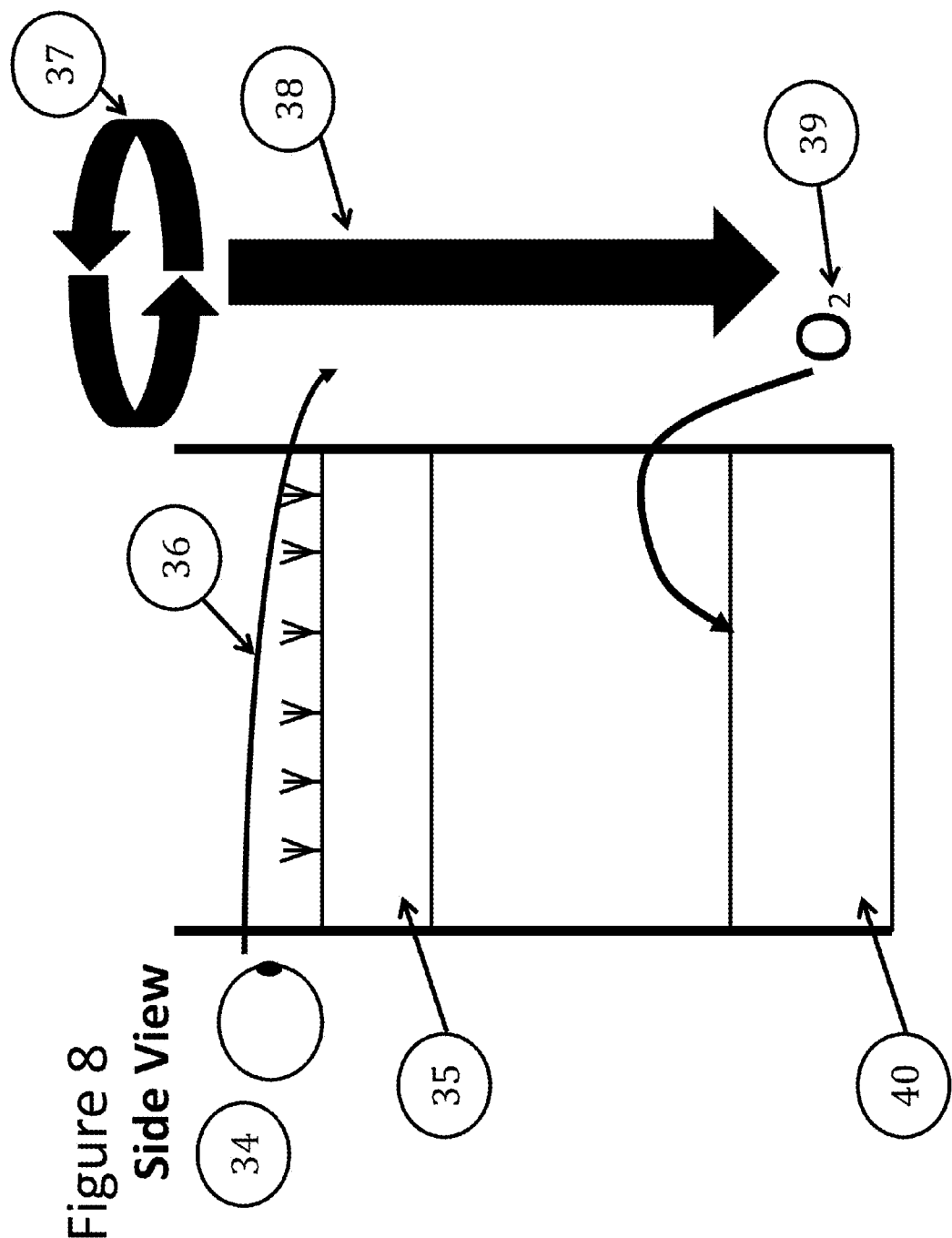
FIG. 8 is a side view of the system including the recapturing of the oxygen according to the disclosure.

One of the features of the system and method according to the present disclosure is the fact that by blowing the carbon dioxide across the hydroponic grow media, the possibility of carbon dioxide dilution with the oxygen is greatly diminished or eliminated. This oxygen can then be recovered and blown back into the hydroponic nutrient tank to oxygenate the nutrient solution. FIG. 8 depicts a full side view of the system used to distribute the carbon dioxide system along with reclaiming the oxygen 39 and using the reclaimed oxygen in aerating the hydroponic nutrient solution. A bubbler in the nutrient tank may be used to introduce the expired oxygen.

In order to maintain optimal levels of carbon dioxide in the system, the hydroponic unit may include a carbon dioxide system controller in communication with a carbon dioxide sensor. When the sensor detects that carbon dioxide levels have dropped below a threshold, additional carbon dioxide may be released. When the sensor detects that carbon dioxide levels have exceeded a threshold, carbon dioxide dispersion may be ceased. Additionally, excess carbon dioxide may be vented. Certain plant species require specific levels of carbon dioxide to achieve optimal growth, such as certain lettuces and basil. The processor may be programmed with a carbon dioxide saturation algorithm to control carbon dioxide levels in accordance with the species being grown in the hydroponic unit, with a growth stage of the plants being grown, a combination thereof, and the like.

In embodiments, the system for carbon dioxide dispersion may be deployed on a rack so that individual racks in a hydroponic unit may each have a local carbon dioxide flow vector that results in a local negative pressure above the rack and re-capture of expired oxygen at the bottom of the rack.

As the plant absorbs carbon dioxide, the resulting oxygen is captured and negative pressure is applied by fans to push the oxygen towards the floor. Once the oxygen is pushed into the floor area, a device picks ups the oxygen and blows it into the hydroponic reservoir tank thus oxygenating the water. Oxygen can be recovered and aspirated back into the hydroponic nutrient tank. FIG. 8 is a full side view of a system used to distribute the carbon dioxide system along with an oxygen reclamation system 39 that recaptures the oxygen and directs the oxygen into the hydroponic nutrient solution.

In embodiments, the hydroponic system is in a sealed container and high pressure $CO_2$ (hyperbaric) is utilized in the environment. In embodiments, to assist with $CO_2$ absorption, it may be beneficial to spray an aqueous solution on the leaves that is saturated with $CO_2$. In embodiments, the partial pressure of nitrogen may be lowered and the partial pressure of $CO_2$ increased in the hydroponic system.

This disclosure also concerns a method and system of optimizing plant cell growth in a hydroponic environment by utilizing low voltage electroculture. This is done by supplying a positive and negative electrical connection into the water medium of the hydroponic solution to excite the plant root structure. The amount of energy provided in the hydroponic water solution varies depending on plant species and the timeline of the growth cycle of the plant.

Electroculture represents a field of study that examines the effects of electricity on plants. As electrical charges work to regulate metabolic processes in cells and tissues, directing electricity into or onto plant structures may further stimulate these same processes. In doing so, plants may become more resistant to cold temperatures, diseases and other pathogens.

The earth has a natural frequency of approximately 8 Hz. It has been found that, by passing a small current though a plant and plant root system at a certain frequency, such as the earth's natural frequency, plant growth and yield can be increased considerably.

Figure 9:
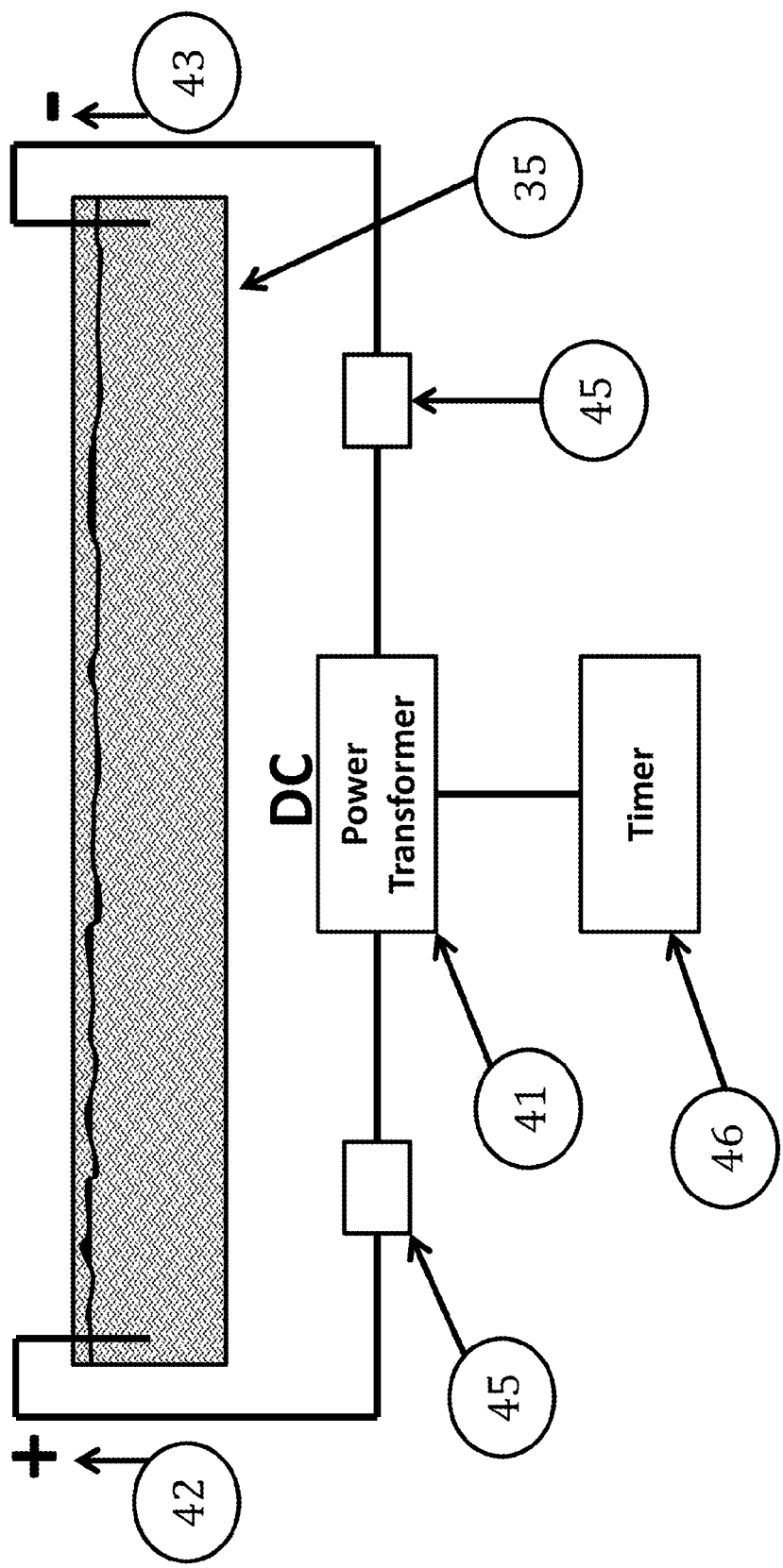
FIG. 9 is a side view of an electroculture system in a hydroponic environment. A wire is inserted at each end of the hydroponic solution and then a current is conducted through the solution to generate an electrical charge in the water.

FIG. 9 describes a system whereby a DC volt transformer 41 is used to conduct a current through a hydroponic growth medium 44 to electrify the nutrient solution at a frequency cycle ranging from 15 to 150 Hz depending upon the plant species and genus.

A frequency meter 45 may be placed on the positive 42 and negative 43 sides of the transformer 41 to measure the outflow and inflow of the electrical current to assure the right frequency cycle is used for a particular plant species.

Timing of the electrical current may correspond with one or more of a lighting profile and a growth profile of the plants in the hydroponic system to provide varied amount and timing of root stimulation. A timer 46 may be attached to the transformer 41 to regulate the timing of the root stimulation. For example, electrical current may only be passed through the liquid nutrient solution at a the time the lighting for the plants is ON. An algorithm may be used in conjunction with a root stimulation profile to apply electrical current.

A method for adjusting the temperature of the nutrient solution of a high density closed loop hydroponic plant growth system is provided. The timing of heating and cooling the nutrient solution is calculated from an equation based upon the seedling growth inside the hydroponic environment along with the power and distance of the grow lighting.

The growing of plants hydroponically involves supplying an aqueous solution to the roots of the plants, for example by spraying solution onto the roots or by keeping them immersed in the liquid solution. The solution is principally water with fertilizers and other nutrients added. Optimal growth, or even survival of the plants, may require that the roots be provided with an air-enriched solution and kept within a specified temperature range. Typically, this is a lower temperature range than required for the portion of the plant above the roots. This parallels the situation in nature where the roots of the plant are in the cooler ground, whereas the upper portions of the plant are in the air that is usually warmer than the ground when the plant is growing.

The hydroponic nutrient solution is not just a mix of fertilizer salts and water, there are also a number of organisms and compounds commonly found in hydroponic systems, such as dissolved oxygen, which is vital for the health and strength of the root system as well as being necessary for nutrient uptake.

Most growers are familiar with the need to have some form of aeration in their nutrient solution—whether it is in a recirculation or a media based system. In nutrient film technique (NFT) systems, this is often accomplished with the use of an air pump or by allowing the nutrients to fall back into the reservoir, thus introducing oxygen. However, the effect of temperature of the solution on the dissolved oxygen levels and on root respiration rates also needs to be taken into account. As the temperature of the nutrient solution increases, the ability of that solution to maintain dissolved oxygen decreases. For example, the oxygen content of a fully aerated solution at 10° C. (50° F.) is about 13 ppm, but as the solution warms up to 20° C. (68° F.) the ability of the liquid to maintain oxygen drops and the oxygen content drops to 9-10 ppm. By the time the solution has reached 30° C. (86° F.), the oxygen content is only 7 ppm.

While this may not seem like a huge drop in the amount of dissolved oxygen, as the temperature of the root system warms, the rate of respiration of the root tissue also increases and more oxygen is required by the plant. For example, the respiration rate of the roots will double for each 10° C. rise in temperature up to 30° C. (86° F.). So a situation can develop where the solution temperature increases from 20°-30° C. (68°-86° F.) during the day, with a mature crop and a large root system, then the requirement for oxygen will double while the oxygen carrying capacity of the solution will drop by over 25%. This means that the dissolved oxygen in solution will be much more rapidly depleted and the plants can suffer from oxygen starvation for a period of time.

The hydroponic growing operation may include a cooling system to cool the aqueous solution before it is fed to the roots of the plant. This cooling system may be separate from the reservoir used to store the solution. In addition, the solution may be aerated to optimize plant growth, such as with a separate aerator. The cooling system may be a condenser placed in or adjacent to the nutrient solution reservoir or throughout the nutrient distribution system. Alternatively, the ambient temperature in the hydroponic unit may be turned down. In any event, temperature sensors may be deployed throughout the hydroponic unit, such as on racks, in the nutrient solution reservoir, in the hydroponic beds, on the floor, on the ceiling, and the like to report back to a processor the temperature of the hydroponic unit, solutions, and the like.

FIG. 10 describes the optimum temperature range for a plant which has a recommended hydroponic nutrient temperature range of "R" 53 for a given plant species.

Equations 47, 48, 49, 50, 51, and 52 describe the different nutrient solution temperatures desired for each plant growth phase based on the recommended hydroponic nutrient temperature "R".

In phase A of the plant's growth life cycle, cooler nutrient solution temperatures are desired while the plant is adjusting to its new liquid environment.

Referring to equation 47 in Phase A1, the hydroponic solution may be cooled to a temperature of 70% of the recommended hydroponic nutrient temperature R.

Referring to equation 48 in Phase A2, the hydroponic solution may be cooled to a temperature of 75% of the recommended hydroponic nutrient temperature R.

Referring to equation 49 in Phase A3, the hydroponic solution may be cooled to a temperature of 80% of the recommended hydroponic nutrient temperature R.

Referring to equation 50 in Phase B, the hydroponic solution may be cooled to a temperature of 100% of the recommended hydroponic nutrient temperature R.

Referring to equation 51 in Phase C, the hydroponic solution may be cooled to a temperature of 100% of the recommended hydroponic nutrient temperature R.

Referring to equation 52 in Phase D, the hydroponic solution may be cooled to a temperature of 70% of the recommended hydroponic nutrient temperature R. In embodiments, the plants may be further chilled before harvest, such as in order to halt or slow cell replication.

In an embodiment, a processor may be programmed with a heating timing algorithm that calculates equations 47-53 and controls a temperature, by either heating or cooling, of the nutrient solution to optimize plant growth. As described previously, determining the actual growth stage may be done by visual analysis or various automated means, such as a video observation, a laser sensor, a location/proximity sensor, a weight measurement, a measurement of an $O_2$ output in the system by an $O_2$ sensor, a measurement of a concentration of a nutrient solution, and the like. The processor may first use the determined growth stage to identify which Phase the plant is in when making optimal temperature calculations. Further, the algorithm may be able to make optimal temperature calculations based on a predicted growth curve for a plant species, given data about when it was planted, and the like. Thus, measurement of plant growth may not be required or may be used to confirm the optimal temperature calculations.

In accordance with the changing temperature in the hydroponic unit, any excess heat may be reclaimed.

In embodiments, the heating and cooling systems of the hydroponic unit enable high temperature growth of sun-sensitive species. For example, lettuce can handle high temperature, but not in sunlight. In the hydroponic unit, lettuce can be grown at high temperature conditions using red and blue light instead of sunlight.

Hydroponics may be described as a method of growing plants or other vegetation without the use of soil and is well-known as such. However, current apparatus operates essentially on a batch system whereas there is a need, particularly in the production, for example of fodder for animals, of a continuous system which will operate independently of the external environment where necessary, to produce a regular and continuous supply of herbage. The present disclosure seeks to provide a method and apparatus for such a continuous system.

In its broadest aspect the present disclosure provides a method that includes taking the seedlings of a desired plant, placing them in a receptacle inside a high density high growth growing system which provides conditions for the growth of the seedlings and growth of the mature plants, and then removing the mature plants from the receptacle. The disclosure further provides an apparatus that includes a series of racks each capable of receiving a receptacle containing plants, each divided into a number of shelves in which the plants may be exposed to the necessary environmental conditions for the particular stage of growth in that zone. The growing system may be a closed environment hydroponic system. Referring now to FIG. 11, a system for growing plants, either from seeds or seedlings, includes a float tray system that provides conditions for growth of seedlings/seeds placed within it, and growth of the eventually mature plants prior to their removal from the receptacle. The system includes a series of racks 55, each capable of receiving plants on a float that is located on a float tray 59. The system also includes an HVAC system 54.

According to the present disclosure there is also provided a receptacle for receiving plants including a tray having a drain hole, the drain hole being fitted with a drain control which includes a drain and tube that returns the nutrient solution from the hydroponic system to the reservoir tank. A pump in the reservoir tank pumps the nutrient solution up to the top of the rack where it is then piped downwards and out to the flood tray. Additionally, the racks that are bolted together are also bolted to the floor with a designed floor plate and braced across with a structural bracing plate.

Referring now to the drawings, and in particular FIG. 11 and FIG. 12, there is illustrated a rack system for receiving plant receptacles. The contained hydroponic system contains racks on both sides of the container. The rack system includes a number of racks 55 installed from right to left and a number of other racks 55 sloping from left to right (as viewed in FIG. 11). The racks may traverse the length of the rack system which is divided lengthwise into a number of zones which are the individual racks described in FIG. 12 and FIG. 13. The apparatus illustrated in FIG. 11 is of a width to allow a rack on both sides of a container, but naturally the width of the apparatus is a matter of choice and it may be made narrower or wider as desired and according to the space available.

Preferred forms of plant receptacles may be a polystyrene float that float in the rack-mounted trays, but in general the plant receptacle may include any tray capable of receiving plants having some form of drain hole to allow spent or excess nutrient or seeds to be removed. Trays containing young plants are entered onto the rack of the apparatus onto the flood tray 59. The apparatus may be divided into four. Each zone is of such a length as to hold a certain number of trays of plants, and in many cases the zones may hold equal numbers of trays of plants. Spacing in the racks may be high density. In one embodiment, there may be 120 mm between growth spaces, but optimal spacing may vary on the species. For example, basil may be spaced at 92 mm.

Trays may pull out from the racks. Trays may be mounted in such a way as to enable easy removal from the rack, such as with sliders, wheels or the like. For mobile embodiments, the racks may include shock absorbers.

FIG. 11 shows a top view of the system whereby the racks are installed on both sides of the container 66 with a space that may or may not be used at one end as a harvest grow room 57. Each rack may be bolted across from each other with a structural beam 65 that prevents the racks from swaying and provides stability in the overall rack design. In embodiments, the rack system may include an HVAC system, a sealed door system 56, and a top rack structural beam system 65.

FIG. 12 and FIG. 13 depict a single rack that may contain six shelves where the flood trays 59 rest upon. The rack includes an attached plumbing design module 61 for pumping nutrient solution up to each of the six shelves into the flood trays from the nutrient fluid reservoir tank. Additionally, return plumbing 63 from the flood trays may be bolted to the opposite side of the rack.

Referring now more particularly to FIG. 12 and FIG. 13, a receptacle for receiving plants may include a variety of different types of float mediums. There may be a central drain orifice at one end of each flood tray with tubing that extends down along the rack and into the nutrient reservoir 63.

In embodiments, as in FIG. 12, the flood trays 59 may be 4 inches high and the total height of the rack may be 8 ft.

The amount, concentration, and type of nutrient solution may be different for each rack according to the growth cycle of the particular plant being grown. Therefore, each of the racks 55 may be supplied from a separate tank of nutrient fluid reservoir 40 which may be pure water or may have growth aiding nutrients or other chemicals within it. The conditions can be selected at each stage in the plant's growth to favor maximum yields.

Carbon dioxide tubing may be installed on the rack system. The carbon dioxide may be blown across the shelving units to provide an increased amount of saturation, as described herein. The amount and pressure of the carbon dioxide in the piping may be selected in accordance with the type of plant species.

The light necessary to induce growth may be provided, for example, by means of fluorescent tubes or LED lights that are mounted to the underside of the shelving unit, as shown in FIG. 15. Alternatively or in addition, the apparatus may be situated so as to receive sunlight either externally or through glass, transparent plastics materials or the like.

Once the system of the disclosure has been set in operation and seedlings have been planted, an apparatus such as those depicted in FIG. 11, FIG. 12, FIG. 13 and/or FIG. 14 may be capable of producing large yields. FIG. 13 is a plan view of a rack system from a vertical view detailing the brace system 64. FIG. 14 is a descriptive view of the rack feet design and its installation to the floor or the hydroponic system, including an L-shaped bracket 67 welded to the floor plate.

FIG. 14 depicts the feet that are attached to the racks that stabilize the entire rack system. A plate is measured to be at least three times the width of the shelving leg width and at least 1.3 times the length of the distance between the racking legs. The feet use an L-shaped bracket that is attached to the bottom plate 67. Additionally, holes are drilled in the plate to allow bolting to the floor 69.

A low profile lighting system may provide more space for growth. In embodiments, the rack-based system in the high growth, high density, growing system may be height-adjustable with high-density spacing, such as to accommodate plant height (e.g. such as for taller romaine lettuce and French tarragon) and optimize lighting distance. Movable racks may allow enough height when approaching maturity while enabling enough power to be delivered at the beginning of growth. Movement may be automated based on height measurement, such as with a laser or video measurement. For example, as growth occurs in the seedlings and is measured, the measurement sensors may feedback to a controller for the movable rack to cause it to be moved further away from the seedling to accommodate growth and/or to reduce the intensity of the light.

For static racks, an optimal light to seedling distance may be calculated. One distance may be eight inches. Optimal lighting placement for LED lighting may optimize plant growth in a high growth, high density, closed environment hydroponic system.

A low voltage growing system may include lighting and mechanical systems connected to a step down transformer that converts high voltage a.c. power to d.c. low voltage power 62. Using a low voltage facilitates the use of solar panels or wind generators to provide electrical power for the unit and enables the use of cheaply and readily available 12v electrical systems and batteries. 12 volt d.c. low voltage lighting and mechanicals are typically specified for two primary purposes in hydroponic environments: 1. The fixtures and mechanicals are generally smaller; and 2. there is a wider variety of beam spreads in the bulbs available for grow lighting. The growing system may be a closed environment hydroponic system.

For the grow lighting, the reason smaller fixtures are possible is simple. Since the filament in the bulb only has to be able to carry 12 volts instead of 120 volts, it can be made much smaller, perhaps ¼" long instead of 1" long for a 120 volt bulb. Since the filament is smaller, the glass bulb around it or the LED can be made smaller, and therefore the fixture can also be designed to be smaller.

The reason more beam spreads are available in a low voltage light is because a small filament or an LED can be aimed much more accurately than a larger one. For applications where light is to be pointed at a specific spot, such as a specific plant, this may be important. The light created at the filament bounces off the reflector and goes in the direction it is pointed. If the glowing filament is very small, very precisely designed reflectors may be used to position the light beam. With a larger filament, it is easy to end up with light beams indiscriminately bouncing.

Certain HID grow lights, for example, with tight beam spreads may be used in much larger scale applications, where great distances from the plant to the light are involved, or less precision is required.

Additionally, low voltage hydroponic mechanical pumps, aerators, and fans are much more reliable and use much less energy than their traditional a.c. voltage counterparts. The average life of d.c. mechanical devices have a notable longer life also.

Most voltage used for hydroponic components are typically 120 a.c. voltage, but can vary between 110 volts and 130 volts. (Standard grow lights are designed to operate at 120 volts. Since 120 volts is standard using a 12 d.c. volt lighting system, a transformer is needed to convert the voltage. This is often a significant part of the cost of a low voltage system.

There are many different "sizes" of transformers available. A small transformer may power a single light, or a giant transformer may power a plurality of lights. There are certain wattage ratings for transformers that have become somewhat standardized.

Transformers are typically run at 80% of their capacity. For example, for powering 100 watts of lights, a transformer rated for at least 120 watts should be used. However, most major manufacturers have already "de-rated" their transformers. This "de-rating" is partly due to the fact that the transformers are not 100% efficient. Some of the capacity of the transformer is used up in its "transforming" function, and some is wasted as heat.

In embodiments, there may be special wiring requirements for low voltage, which simply means that a thicker wire than is typically used in a regular line voltage system is used. One of the biggest advantages of using low voltage wiring in a hydroponic environment is that certain national or local codes require electrical connections to be enclosed in some sort of metal box, and grounded. This is true for low voltage also; however, circuits under 60 watts do not have to meet this requirement. New transformers typically have plastic cases because they have overload and short-circuit breakers built in. Therefore, it may not be necessary to ground the low voltage side of the transformer, only the 120 volt wires coming in to it. Any circuit over 60 watts should be in a metal box.

FIG. 15 describes a side view of the lighting and pump elements of a hydroponic system using a low voltage d.c. system showing the placement of lights 1500 relative to flood trays 59, as well as the reservoir 40 and the step down transformer that converts high voltage a.c. power to d.c. low voltage power 62.

FIG. 16 describes a top view of the wiring design of a 12 volt d.c. system and the placement of the inverter box. The 12 volt dc aerator 44 is connected to the AC to DC inverter box 71 by a 12 volt DC line 72. The d.c. low voltage power 62 is connected to the AC to DC inverter box 71.

FIG. 17 describes a side view of the wiring design of the hydroponic growing system.

This disclosure provides systems and methods for overcoming the adverse effects of root nutrition depletion during hydroponic cultivation when the nutrient solution enters at one end of a hydroponic system and is drained at a second end.

One of the major problems of hydroponic systems is that of uneven nutrient solution feeding to plants in a hydroponic flood tray environment. When plants in a water-based solution start to develop root systems, water tends to flow around the central portion of the flood tray and follow the path of least resistance on the outer parts of the flood tray. Because of this, metabolism of the plants in the nutrient solution immediately around the root system progressively inhibits the uptake of fresh nutrient salts, gases and water, and causes the plants closest to the drain area of the flood tray to receive less nutrients and minerals, thus "starving" a plant.

In static nutrient solutions, this problem is not as extreme. The absorption from the area immediately around the roots and the provision of fresh nutrients and dissolved oxygen to the roots are limited to that which can be achieved naturally and does not create a problem of some plants receiving fewer nutrients than others. This problem can be mitigated or overcome by a method of growing a plant hydroponically which includes supplying nutrient solution to the root of a plant by increasing the pressure and flow of the solution toward the center portion of the flood tray. This, in turn, would provide more solution through the center of the flood tray where the root system of the plant is the densest.

The flow of nutrient solution may be induced by capillarity and takes the form of increased flow of the nutrient solution moving along the surfaces of the interlinked root structure. To take advantage of this supply of nutrient solution the roots of the plants, which are themselves hydrophilic, may develop intimate contact with flow and draw nutrients and water from them at the same rate as the plants on the outer edges of the flood tray. As long as the amount of nutrient solution flowing is greater than that taken up by the root system, there will be a residual flow through and beyond the roots. The results may be obtained when the volume of nutrient solution conveyed to the denser root area in the center of the flood tray is increased approximately 100% in flow rate and pressure.

One important advantage of the system is that it greatly reduces the requirement for consistent balance of the nutrient solution. Since all plants in the flood tray exhibit the same amount of absorption, the nutrient solution is better balanced for control. One of the main attractions of the system is that it enables the plants to maintain vigorous growth over extended periods even in low oxygenated solutions.

Referring to FIG. 18, plants are stationary in a flood tray environment using a variety of grow media. The roots 73 of the plant 74 are denser in the center of the flood tray therefore receive fewer nutrients as the solution is introduced from the entry point 61. However, using the apparatus in FIG. 19, a tube 75 is inserted into the flood tray with small holes of differing sizes, such as hole 76 and hole 80. With the supply line of the solution 61 connected to the tube 75, it provides an evenly distributed environment from which greater solution is pumped over the center plant roots than down the sides.

The number of holes in the apparatus is determined by spacing the holes at ½ inches apart. Since different hydroponic systems have different flow rates, different sized holes may be utilized to find which will provide the best flow and pressure rates for that specific flood tray environment.

In an embodiment, the size and number of holes is determined by a formula, whereby L is the total length of the apparatus called the dispersion bar 79 and the larger center holes will be located along one portion 78 of the total length of the dispersion bar 79, such as a portion that is one half the length of the total bar 78. The diameter of the holes 80 in the center part of the dispersion tube 75 may be four times the diameter (S) 76 of the holes on the outer areas of the dispersion bar. In embodiments, the flow of nutrients across the root system may be from the root tip to the mature root. By providing fresh nutrient solution to the root tip, the hydroponic system is mimicking natural conditions wherein the root tip grows into fresh soil.

A tray pump may pump solution out from the reservoir and into the system. A circulating pump may pull water into the system on one side, but gravity may pull the solution out of the tray and into the tank. The solution circulation system may include a particulate filter (e.g. 0.5 micron filter). Alternatively, solution may be gravity fed from one end and drained at the other end. A back pressure may be created so that downstream plants receive enough nutrients. As the root system gets denser, valves pumping solution may be opened wider. A pipe or screen system may be included in the tray to provide nutrient solution along the length of the tray. Solution may be fed from both ends of the tray to produce turbulent flow. Sensors/flow meters may be deployed in the trays to measure solution flow. Other meters/sensors deployable in the trays include temperature sensor, alkalinity meter, particulate meter, pH sensor, light/UV sensor, moisture sensor on an exterior of the tray or on floors to check for spills/cloggage, nitrate sensor, mass spectrometers, and the like. These sensors/meters may be used to monitor and report on conditions in the hydroponic unit. The sensors may further enable external control and monitoring and aggregate reporting for a plurality of units. Sensors may be distributed for different water systems.

This disclosure also concerns the timing of optimal pH balance for each plant species during its growth cycle. pH is important because it affects availability and absorption of several of the 16 atomic elements needed for plant growth. Maximum absorption of these elements may be found at pH readings 5.5 to 6.5. When pH falls below this range, many of the macro elements (nitrogen (N), phosphorus (P), potassium (K), etc.) may have less availability and absorption of the micro nutrients may reach toxic levels.

Throughout the cycle of plant growth, it has been normally thought that the pH balance for the plant should be steady and constant. Optimal pH's of a nutrient solution for a given plant species is necessary since plants maximize the absorption of elements at different pH levels. Varying pH throughout the growth cycle, as opposed to the steady and constant paradigm, may encourage nutrient absorption of particular elements at different growth cycle stages in a high growth, high density, closed environment hydroponic system.

FIG. 20 describes the different phases of plant growth and the optimal pH level based upon the stage of growth. 'P' is designated as the average plant pH preference 87. This is commonly determined from previous literature and other research for the given plant species. Once that has been determined, the plant's pH may be adjusted in accordance with the current growth phase. The Phase A1 optimal pH 81 is actually higher and may be calculated by multiplying the plant's pH preference by 1. The Phase A2 optimal pH 82 is actually higher and may be calculated by multiplying the plant's pH preference by 1.1. The Phase A3 optimal pH 83 may be the preferred pH. The Phase B optimal pH 84 is actually higher and may be calculated by multiplying the plant's pH preference by 0.6. The Phase C optimal pH 85 is actually higher and may be calculated by multiplying the plant's pH preference by 1.2. The Phase D optimal pH 86 may be the preferred pH. A low pH early in the growth cycle may aid absorption of phosphorus and nitrogen in the seedling stage. Higher, or varied, pH's are optimal for the absorption of certain co-factors and trace elements, such as molybdenum at pH 9. A reticulating nutrient system may support multi-pH irrigations for multi-root plants.

This disclosure concerns an apparatus for controlling the condition of air in an enclosure, and more particularly for controlling the temperature and humidity of air in an enclosure, such as a sealed container for hydroponic plant growth. In embodiments, humidity control may be related to at least one of temperature control and lighting control.

During grow light hours, growing agricultural products introduces water vapor into the air and extracts carbon dioxide from the air. The growth of such products is enhanced when excess carbon dioxide is introduced into the environment during daylight hours. When this water vapor is added to the water vapor products by the growing agricultural products, saturated, or nearly saturated conditions are created within the container. This condition of high humidity produces undesirable stress on all but tropical plants, and increases susceptibility of the plants to various diseases whose control requires periodic spraying or other treatment. As a consequence, considerable resistance has been encountered in applying this approach to plant management.

Referring now to FIG. 21, throughout the cycle of plant growth, dehumidification of the air is desired. However, since this water is considered mineral and salt free, it can be reused as additional water in plant nutrient fluid reservoirs 40. This is accomplished by redirecting the hose assembly 88 from the HVAC system 54 that would normally be directed outside the hydroponic container to drain the excess water into one of the rack reservoirs 40. A climate controller may control the dehumidification process. Avoiding excess moisture that inhibits $CO_2$ from entering chloroplasts may impact plant growth positively. In one embodiment, humidity may be maintained at 65%.

This disclosure concerns slowing down the process of plant cell replication in a growing system by controlling certain environmental factors. The process is determined first by reviewing the amount of the plant cell replication reduction as a variable in terms of percentage and then using an equation to determine what variables are required to be controlled to achieve that desired reduction or acceleration in plant cell replication. The growing system may be a closed environment hydroponic system.

Referring now to FIG. 25, by controlling environmental variables, cell replication may be slowed or accelerated. There may be six or more different environmental control variables: two air temperature settings, two nutrient processes, two grow light settings, and the like. For example, regarding variable A1 118, the air temperature may be reduced to 64° F. In another example, regarding variable A2 119, the air temperature may be reduced to 58° F. In another example, regarding variable B1 120, the nutrient solution may be replaced with water with a 7 pH. In still another example, regarding variable B2 121, the nutrient temperature may be reduced to 64° F. In still another example, regarding variable C1 122, the recommended lighting cycle 124 for a given plant species in a given hours/day may be reduced to one third. In yet another example, regarding variable C2 123, the recommended lighting cycle for a given plant species in a given hours/day may be reduced to one fifth.

Referring to FIG. 24, plant cell replication may be slowed in an approximate range by referring to the percentage decrease in growth. For example, if it is desired to slow the plant cell replication by approximately 30-45% (115), or extend grow time of an 80 day crop another 24 to 36 days (115), using the FIG. 24 table provided, the air temperature of the hydroponic environment would be reduced to below 64 degrees (variable A1 118), the nutrient solution temperature would be reduced to below 64 degrees (variable B2 121), and the recommended lighting cycle for that given plant species would be reduced to one third of the total given hours/day (variable C1 122). In one example, cell replication may be slowed in advance of a harvest. For example, if it is desired to slow the plant cell replication by less than 10% (113), the air temperature of the hydroponic environment would be reduced to below 64 degrees (variable A1 118). For example, if it is desired to slow the plant cell replication by approximately 10-30% (114), the air temperature of the hydroponic environment would be reduced to below 64 degrees (variable A1 118) or below 58 degrees (variable A2 119), and the recommended lighting cycle for that given plant species would be reduced to one third of the total given hours/day (variable C1 122). For example, if it is desired to slow the plant cell replication by approximately 45-80% (116, 117), the air temperature of the hydroponic environment would be reduced to below 64 degrees (variable A1 118), the nutrient solution temperature would be reduced to below 64 degrees (variable B2 121) and/or the nutrient solution can be replaced with pH 7 water (variable B1 120), and the recommended lighting cycle for that given plant species would be reduced to one fifth of the total given hours/day (variable C2 123).

It should be noted that a range is given since different plant species react differently across a spectrum of variables but in general will provide the reduction in the given parameters.

FIG. 23 provides a flow chart such that it gives a guideline from which order the variables are executed in the modulation of the plant cell replication process. Logical flow starts at step 103 and proceeds to an environmental cooling process A 104, a nutrient flush process B 107, and/or a Lighting Process C 110. The environmental cooling process A 104 proceeds to step 105 where the temperature is set. Logical flow may further proceed to step 106 where the temperature is further set to a new setting. The nutrient flush process B 107 proceeds to step 108 where the nutrient solution is flushed out for water. Logical flow may further proceed to step 109 where the temperature of the solution is set to a new setting. The Lighting Process C 110 may proceed to step 111 where the light timing is set to ⅓ of the recommended lighting cycle. Logical flow may continue to step 112 where the light timing is further set to ⅕ of the recommended lighting cycle.

In embodiments, modifying the aforementioned variables may be used in a method of accelerating plant cell growth in a growing system. A combination of one or more of optimizing nutrient solution in accordance with a growth curve, calibrating the pH of the solution to optimize nutrient absorption throughout the growth curve, controlling temperature throughout the growth cycle and at maturation, adjusting the lighting in accordance with a growth stage, and controlling the delivery of carbon dioxide, both in time and in a direction of application, may result in optimized or accelerated cell replication and plant growth. The growing system may be a closed environment hydroponic system.

This disclosure details the type and method of mixing a nutrient solution inside a hydroponic reservoir to provide the correct mixture of nutrients delivered to the plants. Unless proper mixing of the solution in the reservoir is done, the resulting solution may have a stronger concentration in some parts of the reservoir and less in others robbing the plants of the vital nutrients required.

When a hydroponic solution is dispersed over the roots of plants, either through hydroponics or aeroponics, the return nutrient solution usually has a lower concentration of elemental nutrients since the plant absorbs many of these elements. When this solution is returned to the reservoir, there is an imbalance of solution elements that could in turn starve plants if they were continuously recirculated in the system.

To prevent this, there are two methods to correct this problem. Referring to FIG. 26, two mixing pumps 127 are inserted at the end of the return nutrient drain 130 and direct 128 that nutrient solution mixture to be pushed into the other end of the reservoir tank 129 towards the feeding pump 125, which has a supply line 131 to a plant tray. While the nutrient solution is being directed 128 to the other end of the reservoir tank 129, the solution passes over aerators 126 that provide oxygenation to the solution before it is then received by the feeding pump 125.

This method ensures a complete even mixture with the existing nutrient solution in the reservoir tank 129 and provides necessary oxygenation before the nutrient solution is transported to the plants.

One advantage of having multiple mixing pumps 127 and aerators 126 is that it provides a failsafe design in case one of the components fails.

In an embodiment, the nutrient solution includes a hydroponic mix (26/5/5/15), a calcium Nitrate (15/5/0/0), or the like. A lower concentration of nutrient solution may be used for seedlings, then a full concentration may be used later in the growth cycle. Calcium may be added in the middle of the growth curve while nitrate is removed. Boronic copper and zinc may be added as additive to support cell replication. Magnesium and molybdenum may also be added at various points in the growth curve. The nutrient solution may also be ionized in the system.

A nutrient profile may be based on plant growth profile or growth status in a high growth, high density, closed environment hydroponic system This disclosure concerns a hydroponic system whereby hydroponic shelving racks are separated and individual systems are set up in a container to isolate and reduce the potential of pathogenic and bacteria risk that may occur in the hydroponic plant production process.

By building a continuous yet individual and separate hydroponic system for each rack in a container environment, the risk of bacteria or pathogen infection in the nutrient solution, shelving units, or air is reduced thereby preventing an entire production plant crop from being subjected to destruction. A distributed solution delivery system provides isolation from contamination in a high growth, high density, closed environment hydroponic system.

FIG. 27 is a side view of a hydroponic container consisting of a number of hydroponic shelving racks. Each rack is labeled and is considered an independent grow system from each of the other racks 133 to 137. Each unit may have a plurality of racks, such as ten racks, and each rack may hold a plurality of trays, such as six trays. Rack 133 is used in an exemplary fashion to illustrate the isolation process between each of the racks.

Each rack contains a number of flood trays 141 on the rack. The nutrient solution resides in the reservoir 143 and is pumped only to the flood trays above the reservoir tank via a feeding pump 139 and pumped through the hydroponic piping 138 and then the nutrient solution is distributed downward to each flood tray 141. The nutrient solution is then received into a drain hole at the opposite end of the flood tray and a hose 140 from each rack is directed downward back into the reservoir tank 143. Once the nutrient solution reaches the reservoir tank, a series of mixing pumps 142 mix the return nutrient solution with the existing solution in the tank.

Each rack may use one dedicated reservoir to minimize the impact of accidents with pathogens or contaminants, but also enables selectivity as to what each rack receives.

Other ways of reducing contamination in the hydroponic system include placing a UV light into reservoir, using HEPA filters for air scrubbing, using anti-microbial coating on surfaces, using anti-microbial paint on floors, using an electronic scrubber to ionize the air and remove electrostatic particles that do not support photosynthesis, using an alcohol to decontaminate the system, using a filter on the circulation pump, and the like.

Filling the reservoir may be done in the presence of a Charcoal filter.

A growing system may utilize LED lighting. The growing system may comprise a container, a shelving rack, and flood trays whereby the LED lights provide all the lighting necessary for the growth of a specific plant species. The growing system may be a closed environment hydroponic system. The container may be a hydroponic container.

Figure 28:
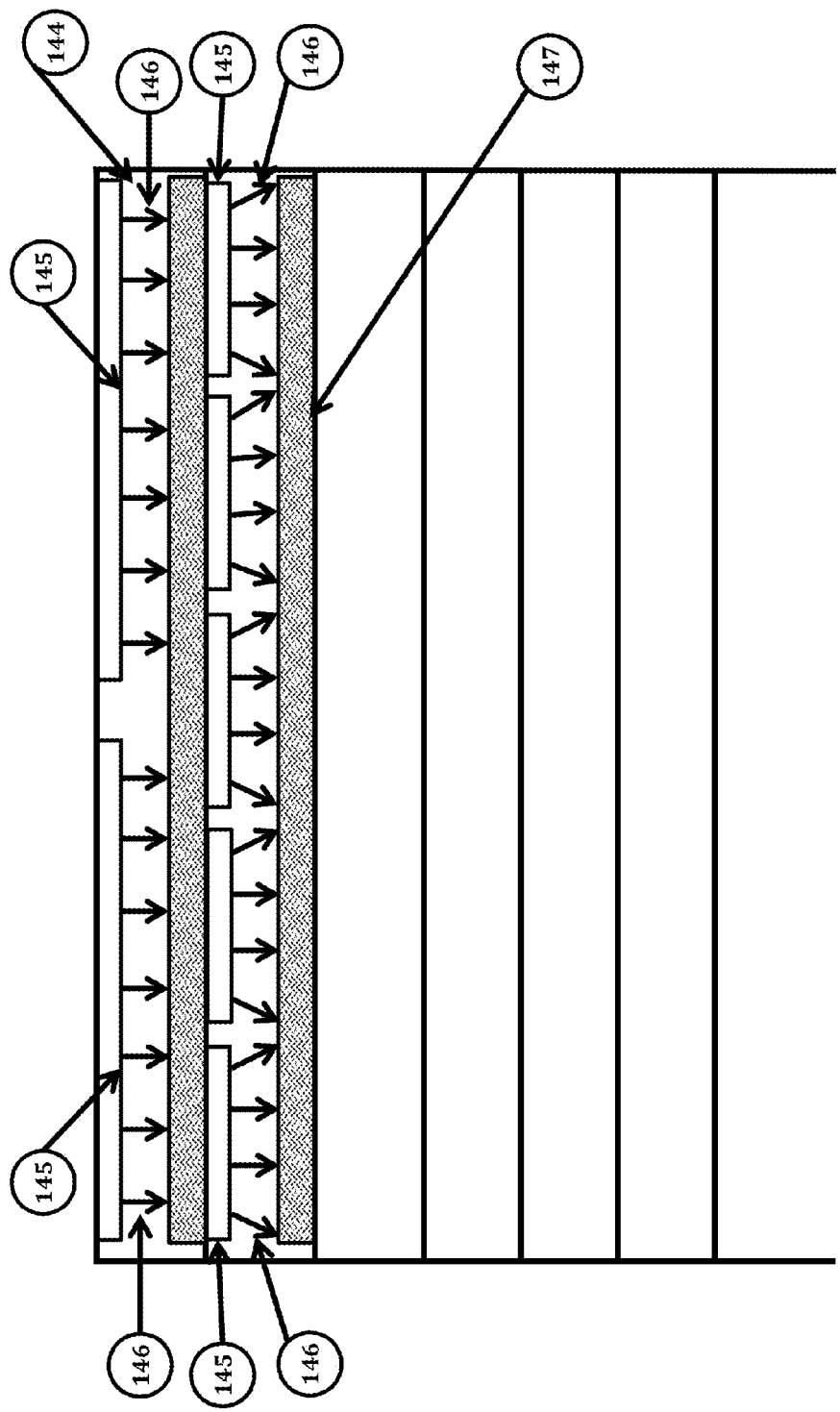
FIG. 28 depicts a single rack with LED lights.

FIG. 28 depicts a rack 144 with LED lights 145, either in a row or box design whereby the light emission 146 is downward upon the flood tray 147.

FIG. 29 outlines the suggested wattage per square foot ($R_W$) and the placement of LED lights with a total coverage factor of red LED versus the blue LED and the wavelengths suggested for a given plant species. In an embodiment, $R_W$ may be 25 watts for Red/Blue LED. In one embodiment, the Red LED may be 640 Nm to 720 Nm and may account for 81% of the LED lights. In one embodiment, the Blue LED lights may be 400 Nm to 480 Nm and may account for 19% of the LED lights. In an embodiment, the red LEDs may account for a greater proportion of the LEDs than the blue LEDs.

LED lights may have a damp-proof housing. The housing may include sealing materials. The housing may include polyfilm plexiglass that allows LED light to be transmitted. An anti-reflective coating may reduce the reflection off the plexiglass.

The LEDs may be dimmable. LEDs may be dimmed in accordance with a growth curve.

LEDs may include a lens that changes the optical profile of the LED based on a growth stage. For example, as the plant matures and grows, the optics may be changed to spread the light.

The hydroponic unit may be housed in a mobile facility, such as a shipping container or truck trailer. Such units may be scalable. Such units may be useful for emergency and disaster response. The hydroponic unit may be housed in a dedicated building or may be housed in buried concrete blocks. The movable, scalability of the units makes it attractive for a variety of deployment scenarios, such as a mobile unit, an on-site growth environment such as integrated into a retail store or farmer's market, or the like. In one embodiment, while the unit is being transported, plants may be growing within. The system may be able to displace transportation elements in supply chain by growing on-site or at strategic sites based on market needs. The flexibility of the unit may enable it to meet spot market needs. The unit may be integrated with food production systems for value-added foods (e.g., mixes; prepared food systems).

The exterior of the unit may have reflective (or PV absorptive) technology, such as when deployed in high UV areas. Ingress and egress may be tightly controlled, such as with a sealing door, optionally including a slider system. The unit may include controls to track the status of sealing over time. The unit may include a dual door system, such as found in a clean room/holding area/air lock. Facial recognition may be used as a security method for ingress. Bar code or UPC labeling may be used for tracking plants throughout the lifecycle. The bar codes may be used on a per-rack, per shelf, per unit, per tray or per plant basis.

The hydroponic system may be used to produce retail or commercial produce.

A shelf elevator may be used in the unit to elevate items onto the racks. A shelf footing system may be used to stabilize the racks.

In an embodiment, a renewable/clean power source, or dedicated power, such as mini- or micro-cogen units, may be integrated with the high growth, high density, closed environment hydroponic system. Power systems useful by the hydroponic system include grid, solar (off-grid), wind, hybrid systems, biodiesel generator, mini- or micro-cogeneration units, and the like. In one example, 8.5 kW of power is needed to run the lighting and heating.

A retooling method after harvest for a system for a high growth, high density, closed environment hydroponic system may include a chlorine dioxide cleanup system followed by HEPA filtration to remove the chlorine dioxide, decontamination of the system, such as with alcohol, vodka, or other decontaminate, draining water, refilling with refreshed de-ionized water, and replanting.

Figure 22:
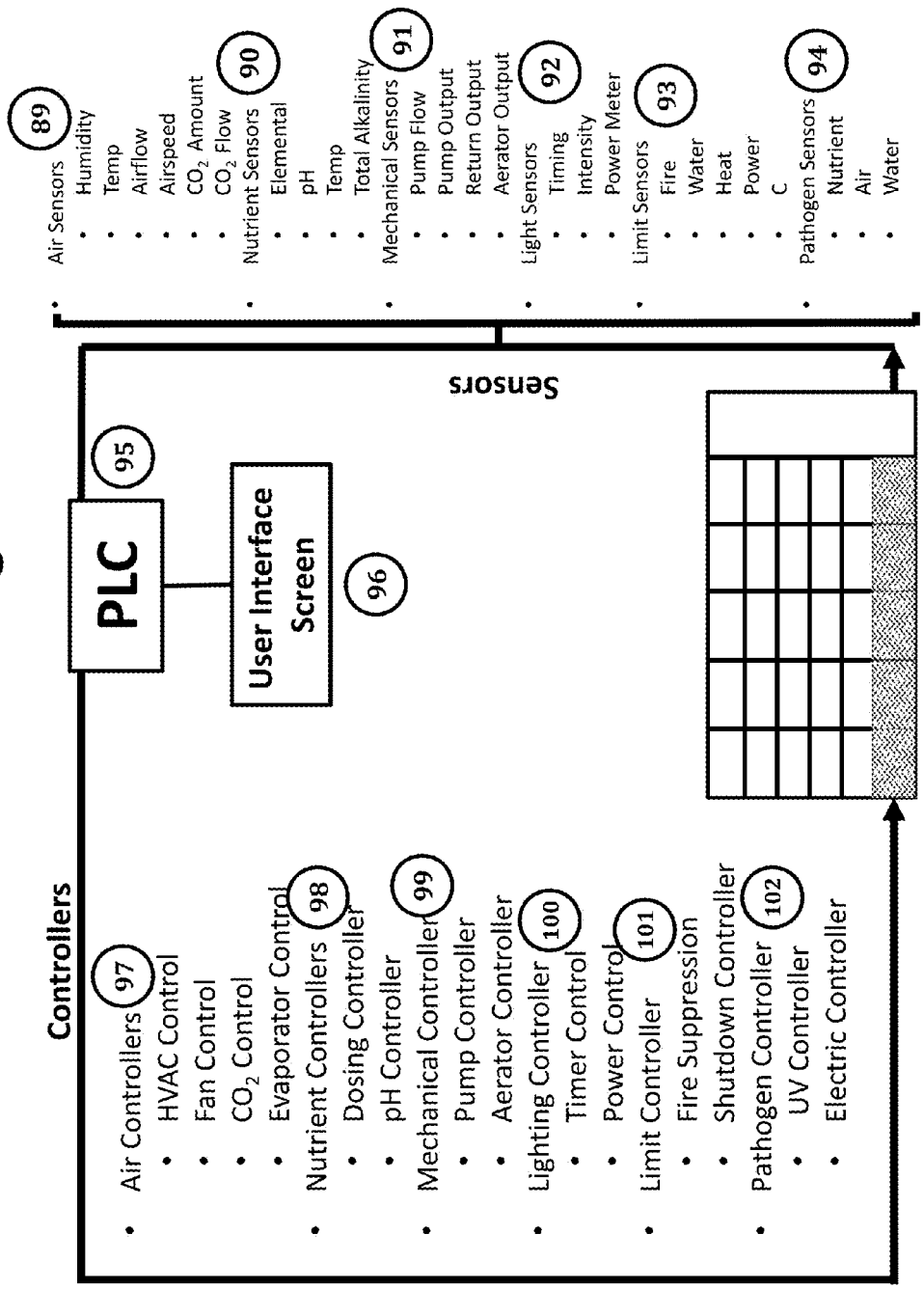
FIG. 22 depicts a PLC controlling the hydroponic unit.

Referring now to FIG. 22, a PLC 95 may enable automatic control of all functions of the growing system, which may be a hydroponic growing system, using controllers, such as Air Controllers 97 (HVAC Control, Fan Control, $CO_2$ Control, Evaporator Control), Nutrient Controllers 98 (Dosing Controller, pH Controller), Mechanical Controllers 99 (Pump Controller, Aerator Controller), Lighting Controllers 100 (Timer Control, Power Control), Limit Controllers 101 (Fire Suppression, Shutdown Controller), Pathogen Controllers 102 (UV Controller, Electric Controller), water flow controller, and the like. The controllers may obtain data from one or more sensors that assist in determining a control needed. The sensors may include Air Sensors 89 (Humidity, Temp, Airflow, Airspeed, $CO_2$ Amount, $CO_2$ Flow), Nutrient Sensors 90 (Elemental, pH, Temp, Total Alkalinity), Mechanical Sensors 91 (Pump Flow, Pump Output, Return Output, Aerator Output), Light Sensors 92 (Timing, Intensity, Power Meter), Limit Sensors 93 (Fire, Water, Heat, Power, C), Pathogen Sensors 94 (Nutrient, Air, Water), and the like. A user interface 96 may be used to input preferences, rules, review reports, review monitoring data, adjust controls, and the like. For example, users may be able to monitor multiple systems, do external/remote monitoring, do unit reporting, do aggregate unit reporting, and the like. Container and rack-based reporting may include information on the contents, growth status, timing, alerts (e.g. contamination, problems with growth, safety), location, status of entry/egress, entry/egress log, pathogen reporting, sealing status, and the like. The system may include a contamination controller and sensor, an air lock control, a pathogen controller and sensor, and the like. The controls/sensors may be in-line with an HVAC system and may set off an alarm when there is contamination present.

In an embodiment, the hydroponic system enables produce to be produced in a high growth, high density, closed environment hydroponic system and delivered without human hands ever touching it and without herbicide and/or pesticide treatment during growth, harvest or transportation phase. The resultant product may have a long shelf life.

Exemplary plants that can be grown in the hydroponic unit include carrot greens, lettuces, buttercrunch lettuce, red line lettuce, romaine, black seeded simpson, bistro blend, salad bowl, oak leaf, red leaf, kale, red Russian kale, collard greens, escarole, bok Choy, cannabis, dill, French tarragon, mint, parsley, cilantro, rosemary, lavender, mustard, watercress, microgreens, basil, arugula, spinach, chives, sunflowers, wheatgrass, stevia, anti-oxidant rich plants, oil plants, soybean, algae, flax, camelina, crambe, thyme, oregano, herbs, flowers, and the like.

Algorithms may be executed by a system-associated processor to optimize growth/energy consumption, track $O_2$ movement, deliver/reclaim water, handle all aspects of nutrition, utilize sensor data to control a system function, iteratively determine a control sequence such as with a machine learning system, provide simulation-based control, perform a market optimization (prices, inputs, outputs), determine and execute a nutrient schedule, such as one based on a condition such as calcium deficiency or one based on a profile.

Data from the system may be used in making a price prediction for the products. Data may feed into a spot produce market to instantly locate available buyers and negotiate prices.

Data from the system may be used in predictive analytics (e.g. Growth prediction), Growth cycle analysis, Event analysis (failure modes, Pathogen monitoring), performing a historical analysis of all controlled variables at rack level for entire growth cycle, perform growth modeling and statistics, generate computer simulation models (tool kit), and the like.

The methods and systems described herein may be deployed in part or in whole through a machine that executes computer software, program codes, and/or instructions on a processor. The processor may be part of a server, cloud server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, cloud servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, cloud servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

The above systems and methods have been described in the context of a hydroponic system. It is to be understood that these systems and methods apply equally to methods and systems which employ soil to grow plants. Many of these systems and methods may incorporate soil into the racks holding the plants and also result in the benefits described for the hydroponic systems and methods.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

All documents referenced herein are hereby incorporated by reference.

What is claimed is:

1. A growing system for promoting the rapid growth of a plurality of seedlings, comprising:
   a substantially closed container for one or more seedlings of the plurality of seedlings;
   a nutrient solution within the closed container;
   a first seedling positioned within the nutrient solution;
   a grow light;
   at least one sensor adapted to observe growth of the first seedling; and
   a controller coupled to the grow light and the at least one sensor, the controller programmed to:
   read information from the sensor to determine when growth has occurred;
   calculate a seedling stress duration, wherein the seedling stress duration commences with the positioning of the first seedling in the growing system and terminates when growth is observed in the first seedling;
   divide the seedling stress duration into a plurality of subphases;
   determine a subphase factor for each of the plurality of subphases for a second seedling positioned in the growing system based on which subphase of the plurality of subphases the second seedling has reached based on an elapsed time;
   calculate a total number of on/off light cycles and a duration for each on/off cycle, wherein one cycle is turning the lights on and off; and
   control the grow light to execute the total number of calculated on/off light cycles for the calculated duration of time the lights are on and time the lights are off during each cycle in the growing system.

2. The growing system of claim 1, wherein the subphase factor for each of the plurality of subphases comprises a fraction of the seedling stress duration.

3. The growing system of claim 1, wherein the number of on/off light cycles comprises twice the subphase factor for each of the plurality of subphases.

4. The growing system of claim 1, wherein the plurality of subphases comprises three subphases.

5. The growing system of claim 1, wherein there are three subphases and the fraction for a first subphase is $\frac{1}{600}$.

6. The growing system of claim 1, wherein there are three subphases and the fraction for a second subphase is $\frac{1}{300}$.

7. The growing system of claim 1, wherein there are three subphases and the fraction for a third subphase is $\frac{1}{200}$.

8. The growing system of claim 1, wherein the grow light is at least one of a red LED light and a blue LED light.

9. The growing system of claim 1, wherein the grow light is of a wavelength selected in accordance with a predetermined plant species.

10. The growing system of claim 1, wherein the controller is further programmed to divide the rapid growth into the plurality of subphases followed by one or more phased periods, the one or more phased periods used to calculate on/off times and cycles that are different for each of the one or more phased periods.

11. The growing system of claim 1, wherein the sensor to monitor growth of a plant is one or more of a video observation, a laser sensor, and a location/proximity sensor.

12. The growing system of claim 1, further comprising a scale for measuring a weight of the first seedling.

13. The growing system of claim 1, wherein the sensor to monitor growth of a plant is an $O_2$ sensor.

14. The growing system of claim 1, further comprising a $CO_2$ sensor for measuring an atmospheric $CO_2$ concentration in an atmosphere above one or more of the plurality of closed containers.

15. The growing system of claim 1, wherein the growing system is a hydroponic growing system.

16. A growing system for promoting the rapid growth in stages of a plurality of seedlings, comprising:
    a substantially closed container for one or more seedlings of the plurality of seedlings;
    a nutrient solution within the closed container;
    a first seedling positioned within the nutrient solution;
    a grow light; and
    a controller coupled to the grow light, the controller programmed to:
    receive information on a growth of the first seedling;
    calculate a seedling stress duration, wherein the seedling stress duration commences with the positioning of the first seedling in the growing system and terminates when growth is observed in the first seedling;
    divide the seedling stress duration into a plurality of subphases;
    determine a subphase factor for a second seedling positioned in the growing system based on which subphase the second seedling has reached based on an elapsed time;
    calculate a total number of on/off light cycles and a duration for each on/off cycle, wherein one cycle is turning the lights on and off; and
    control the grow light to execute the total number of calculated on/off light cycles for the calculated duration of time the lights are on and time the lights are off during each cycle in the growing system.

17. The growing system of claim 16, wherein the grow light comprises a plurality of red lights and blue lights, and the controller is programmed to deliver a desired ratio of red light to blue light to the plurality of seedlings.

18. The growing system of claim 16, wherein the grow light comprises a plurality of lights or LED lights and the controller is programmed to deliver one or more specific wavelengths of light to the plurality of seedlings.

19. The growing system of claim 16, wherein the controller is programmed to control a single, fixed 24-hour on/off light cycle for the grow light after the plurality of subphases.

20. The growing system of claim 19, wherein an on portion of the single, fixed on/off light cycle comprises one-half a recommended on time during a final subphase of the plurality of subphases.

\* \* \* \* \*

UNITED STATES PATENT AND TRADEMARK OFFICE
CERTIFICATE OF CORRECTION

PATENT NO. : 9,565,812 B2
APPLICATION NO. : 14/200210
DATED : February 14, 2017
INVENTOR(S) : James G. Wilson It is certified that error appears in the above-identified patent and that said Letters Patent is hereby corrected as shown below:

In the Specification

Column 3, Line 46, after "species" insert -- . --.

Column 14, Line 24, after "at" delete "a".

Column 24, Line 37, after "system" insert -- . --.

Column 25, Line 27, delete "($R_W$)" and insert -- ($R_w$) --, therefor.

Column 25, Line 29, delete "$R_W$" and insert -- $R_w$ --, therefor.

Column 26, Line 27, delete "decontaminate," and insert -- decontaminant, --, therefor.

Signed and Sealed this
Sixth Day of March, 2018

Andrei Iancu
*Director of the United States Patent and Trademark Office*